(12) United States Patent
Lee et al.

(10) Patent No.: US 9,078,912 B2
(45) Date of Patent: Jul. 14, 2015

(54) ASTHMA DIAGNOSIS USING THE NEUROPILIN-1 GENE, AND METHOD FOR SCREENING FOR A THERAPEUTIC AGENT FOR ASTHMA

(75) Inventors: Hyeong Kyu Lee, Daejeon (KR); Kyung Seop Ahn, Daejeon (KR); Yoosik Yoon, Seoul (KR); Byoung Whui Choi, Seoul (KR); Ok-Kyoung Kwon, Daejeon (KR); Semi Kim, Daejeon (KR); Hui Seong Kim, Daejeon (KR); Sei Ryang Oh, Daejeon (KR); Ji Eun Yuk, Daejeon (KR); Ha Young Jang, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/807,829

(22) PCT Filed: Jul. 1, 2011

(86) PCT No.: PCT/KR2011/004864
§ 371 (c)(1),
(2), (4) Date: Dec. 31, 2012

(87) PCT Pub. No.: WO2012/002775
PCT Pub. Date: Jan. 5, 2012

(65) Prior Publication Data
US 2013/0108652 A1    May 2, 2013

(30) Foreign Application Priority Data
Jul. 2, 2010   (KR) ........................ 10-2010-0063905

(51) Int. Cl.
*A61K 39/395* (2006.01)
*C12N 15/11* (2006.01)
*A61K 31/7088* (2006.01)
*C07K 14/71* (2006.01)
*C12Q 1/68* (2006.01)

(52) U.S. Cl.
CPC ......... *A61K 31/7088* (2013.01); *A61K 39/3955* (2013.01); *C07K 14/71* (2013.01); *C12Q 1/6883* (2013.01); *C12Q 2600/156* (2013.01); *G01N 2800/122* (2013.01); *G01N 2800/24* (2013.01)

(58) Field of Classification Search
None
See application file for complete search history.

(56) References Cited

U.S. PATENT DOCUMENTS

2006/0115477 A1*  6/2006  Unger et al. ............... 424/145.1
2008/0213268 A1*  9/2008  Watts et al. ................ 424/137.1

FOREIGN PATENT DOCUMENTS

EP          1221618         7/2002
WO      WO 9955855 A2  *  11/1999
WO      WO 2010054221 A2  *  5/2010

OTHER PUBLICATIONS

Karjalainen et al, Targeting neuropilin-1 in human leukemia and lymphoma, Jan. 2011, Blood, vol. 117, No. 3, 920-927.*
Neugebauer et al, Identification and differentiation of single cells from peripheral blood by Raman spectroscopic imaging, May 2010, Journal of Biophotonics, 3, No. 8-9: 579-587.*
Elena Geretti, et al., Novel Targets for Anti-Angiogenesis Therapies, Cell adhesion and Migration, vol. 1 (2), pp. 56-61, 2007.
Glenn P. Dorsam, et al., Gene Expression Profiling and Network Analysis . . . , Microbiology and Immunology, vol. 54(9), pp. 558-563, 2010.
Dunja Bruder, et al., Neuropilin-1: A Surface Marker of Regulatory T Cells, Eur. J. Immunol., vol. 34 (3), pp. 623-630, 2004.
Johanna E. Korf, et al., Macrophage Reprogramming by Mycolic Acid Promotes . . . , Am. J. Respir Crit Care Med., vol. 174, pp. 152-160, 2006.

* cited by examiner

*Primary Examiner* — Tracy Vivlemore
*Assistant Examiner* — Kate Poliakova
(74) *Attorney, Agent, or Firm* — Lucas & Mercanti, LLP

(57) ABSTRACT

The present invention relates to a kit for the diagnosis or screening of asthma comprising neuropilin (NRP) gene, and to a method for screening a therapeutic agent for asthma using the same. More precisely, the present invention confirmed that NRP1 expression was increased in asthma patients and by *D. pteronissinus* extract. Based on the confirmation, the inventors confirmed that NRP1 could be effectively used as a target for the development of a therapeutic agent for asthma since the suppression of NRP1 expression resulted in the decrease of mRNA, protein, enzyme activity, and promoter activity of MMP-9 in relation to asthma.

5 Claims, 13 Drawing Sheets

(A)

(B)

(C)

SEQUENCE LISTING

<160> NUMBER OF SEQ ID NOS: 11

<210> SEQ ID NO 1
<211> LENGTH: 572

```
<212> TYPE: DNA
<213> ORGANISM: Homo sapiens

<400> SEQUENCE: 1
ctttgaactt gtggatggtg tgaagttgaa aaaagacaaa ctgaatacac agagtactta      60
ttcggaggca tgaaggcaga cagagatgaa aagacagtca aaggacggaa gtggaaggac     120
gggagtgagc tggggagctg ttgatctttc actatacagg ctgggaagtg tgttgatgac     180
cactgagcca ggcttttctc aggagcttca atgagtatgg ccgacagaca tggacaagga     240
gctgtgttca ccatcggact catgtgcagt cagctttttt cctgttggtt tcatttgaat     300
aatcagatgc tggtgttgag accaagtatg attgacataa tcattcattt cgaccccctcc    360 tgcccctctc tctctctctc ctctccccctt tgtggattct ttttggaaac tgagcgaaat    420
ccaagatgct ggcaccaagc gtattccgtg tggccctttg gatggacatg ctacctgaaa    480
cccagtgccc agaatatact agaatcaccg catttcagtg gactcctgaa gttgtacttg    540
tgtataattg cccgcgtcgt gcataggcaa ag                                   572

<210> SEQ ID NO 2
<211> LENGTH: 20
<212> TYPE: DNA
<213> ORGANISM: Artificial Sequence
<220> FEATURE:
<223> OTHER INFORMATION: NRP1 forward primer for pcr

<400> SEQUENCE: 2
ccacagtgga acaggtgatg                                                  20

<210> SEQ ID NO 3
<211> LENGTH: 20
<212> TYPE: DNA
<213> ORGANISM: Artificial Sequence
<220> FEATURE:
<223> OTHER INFORMATION: NRP1 reverse primer for pcr

<400> SEQUENCE: 3
gcacgtgatt gtcatgttcc                                                  20

<210> SEQ ID NO 4
<211> LENGTH: 28
<212> TYPE: DNA
<213> ORGANISM: Artificial Sequence
<220> FEATURE:
<223> OTHER INFORMATION: MMP9 forward primer for promoter cloning

<400> SEQUENCE: 4
gatcctcgag ctagaggctg ctacttgc                                         28

<210> SEQ ID NO 5
<211> LENGTH: 28
<212> TYPE: DNA
<213> ORGANISM: Artificial Sequence
<220> FEATURE:
<223> OTHER INFORMATION: MMP9 reverse primer for promoter cloning

<400> SEQUENCE: 5
gatcaagctt tctgactgca gctgctgt                                         28

<210> SEQ ID NO 6
<211> LENGTH: 21
<212> TYPE: DNA
<213> ORGANISM: Artificial Sequence
<220> FEATURE:
```

-continued

```
<223> OTHER INFORMATION: siRNA target primer of NRP1

<400> SEQUENCE: 6
ctgcacaaat ctctgaaact a                                              21

<210> SEQ ID NO 7
<211> LENGTH: 70
<212> TYPE: DNA
<213> ORGANISM: Artificial Sequence
<220> FEATURE:
<223> OTHER INFORMATION: Forward primer for NRP1 siRNA

<400> SEQUENCE: 7
gatcccgtag tttcagagat tgtgcagtt gatatccgct gcacaaatct ctgaaactat     60
tttttccaaa                                                           70

<210> SEQ ID NO 8
<211> LENGTH: 70
<212> TYPE: DNA
<213> ORGANISM: Artificial Sequence
<220> FEATURE:
<223> OTHER INFORMATION: Reverse primer for NRP1 siRNA

<400> SEQUENCE: 8
agcttttgga aaaatagtt tcagagattt gtgcagcgga tatcaactgc acaaatctct     60
gaaactacgg                                                           70

<210> SEQ ID NO 9
<211> LENGTH: 20
<212> TYPE: DNA
<213> ORGANISM: Artificial Sequence
<220> FEATURE:
<223> OTHER INFORMATION: scrambled siRNA

<400> SEQUENCE: 9
ggcgcgcttt gtaggattcg                                                20

<210> SEQ ID NO 10
<211> LENGTH: 66
<212> TYPE: DNA
<213> ORGANISM: Artificial Sequence
<220> FEATURE:
<223> OTHER INFORMATION: Forward primer for scrambled RNA

<400> SEQUENCE: 10
gatcccgcga atcctacaaa gcgcgcttga tatccggcgc gctttgtagg attcgttttt    60
tccaaa                                                               66

<210> SEQ ID NO 11
<211> LENGTH: 66
<212> TYPE: DNA
<213> ORGANISM: Artificial Sequence
<220> FEATURE:
<223> OTHER INFORMATION: Reverse primer for scrambled RNA

<400> SEQUENCE: 11
agcttttgga aaaacgaat cctacaaagc gcgccggata tcaagcgcgc tttgtaggat     60
tcgcgg                                                               66
```

ASTHMA DIAGNOSIS USING THE NEUROPILIN-1 GENE, AND METHOD FOR SCREENING FOR A THERAPEUTIC AGENT FOR ASTHMA

CROSS-REFERENCE TO RELATED APPLICATIONS

This application is a 371 of PCT/KR2011/004864, filed on Jul. 1, 2011, which claims the benefit of Korean Patent Application No. 10-2010-0063905 filed on Jul. 2, 2010, the contents of which are incorporated herein by reference.

BACKGROUND OF THE INVENTION

1. Field of the Invention

The present invention relates to a use of NRP1 gene as a target for the development of an asthma marker or a therapeutic agent for asthma.

2. Description of the Related Art

Anaphylaxis, allergic rhinitis, asthma, atopic dermatitis, and urticaria are the examples of allergic diseases whose incidence rates have been increased world-widely (Wuthrich B. Int. Arch. Allergy Appl. Immunol., 90, pp 3-10, 1989). Among the said allergic diseases, asthma is characterized by bronchial hyperresponsiveness, which leads to chronic airway inflammation with carrying such symptoms as wheezing, dyspnea, and cough which are caused by extensive narrowness of the airway. Asthma can be reversed or improved naturally or by treatment (Minoguchi K and Adachi M. Pathophysiology of asthma. In: Chemiack N S, Altose M D, Homma I, editors. Rehabilitation of the patient with respiratory disease. New York: McGraw-Hill, pp 97-104, 1999).

Asthma is generally recognized as chronic inflammatory disease which is caused by the migration and infiltration of inflammatory cells proliferated, differentiated, and activated by interleukin-4, 5, and 13 generated by TH2 immunocytes into and around the airway (Elias J A, et al., *J. Clin. Invest.*, 111, pp 291-297, 2003). At this time, the activated inflammatory cells such as eosinophils, mast cells and alveolar macrophages secret various inflammation mediators (cysteinyl leukotriene, prostaglandin, etc), which play a critical role in bronchoconstriction (Maggi E., *Immunotechnology,* 3, pp 233-244, 1998; Pawankar R., *Curr. Opin. Allergy Clin. Immunol.,* 1, pp 3-6, 2001; Barnes P J, et al., *Pharmacol Rev.,* 50, pp 515-596, 1998).

Productions of cytokines involved in the activation of inflammatory cells such as IL-4, IL-5, and IL-13, and immunoglobulin E, as well as biosynthesis of cysteinyl leukotriene secreted from inflammatory cells such as eosinophils mediated by the said cytokines and immunoglobulin E are regarded as major reasons of inflammation and allergic reaction and further asthma caused by such inflammation and allergic reaction. Therefore, studies are actively undergoing to develop drugs to inhibit the productions of the said cytokines, immunoglobulin E, and cysteinyl leukotriene. In particular, to understand on the allergic disease including asthma and rhino conjunctivitis, animal models have been used for the study. Animal models not only help the understanding of immunological mechanism in relation to allergic reaction but also enable the evaluations of novel drugs under development.

Neuropilin (NRP) consists of Neuropilin 1 and Neuropilin 2. Neuropilin 1 and Neuropilin 2 were first found in neurons (Takagi S et al., Dev Biol, 1987). Since then, they were identified as semaphorin 3A (SEMA3A) receptors mediating axon guidance with inhibiting the expression not in axons but in Growth cones (He Z, Cell, 1997). And then, the role of NRP as vascular endothelial growth factor (VEGF) family receptor known to be involved in angiogenesis receptor has been disclosed (Soker S et al., Cell, 1998).

NRP is a single transmembranal glycoprotein having the molecular weight of 130~140 kDa. NRP1 is composed of approximately 923 amino acids and NRP2 is composed of approximately 926 amino acids. They both have similar domain structure with overall 44% amino acid homology (Caroline PELLET-MANY et al., Biochem J., 2008).

NRP1 and NRP2 are expressed in a variety of human tumor cell lines and human neoplasms (Bielenberg, D. R et al, Exp. Cell Res, 2006; Soker, S. et al, Cell, 1998; Ellis, L. M., Cancer Ther, 2006). It has been known that they are involved in the activities of VEGF and semaphorin affecting proliferation, survival, and migration of cancer cells (Bachelder, R. E. et al, Cancer Res, 2001; Chabbert-de Ponnat et al, J. Invest. Dermatol., 2006; Miao et al, FASEB J., 2000). NRP1 is found in the samples of patients with colon cancer, breast cancer, lung cancer, prostatic cancer, and pancreatic cancer, but not found in normal epithelium tissues. NRP1 is also found in various tumors such as neuroblastoma, melanoma, and astrocytoma. NRP2 is found in lung cancer, neuroblastoma, ostersarcoma, pancreatic cancer, and bladder cancer, according to previous reports. NRP1 is also expressed in a variety of cells including bone marrow derived progenitor cells, bovine granulosa platelets, granulosa cells, and theca cells, etc (Caroline PELLET-MANY et al, Biochem J., 2008). NRP1 is expressed in naïve T-cells and immature antigen-presenting cells, and is essential to induce the proliferation and differentiation of mature T-cells reacting with antigen-presenting cells mediating antigen elimination after the first immune response in the secondary lymphoid organs (Matthies, A. M., et al, Am. J. Pathol., 2002).

According to other reports, NRP1 is over-expressed by tissue wound healing reaction, suggesting that NRP1 is involved in regeneration and recovery. When optic nerve is damaged and needs to be regenerated in *Xenopus*, NRP1 expression is increased and even after healing, NRP1 up-regulation continues for further several weeks (Matthies, A. M., et al, Am. J. Pathol., 2002). NRP1 is found in a large scale in wound angiogenesis. Wound angiogenesis is reduced by anti-NRP1 antibody, suggesting that NRP1 plays an important role in angiogenesis (Elena Gerettil et al, Cell Adhesion & Migration, 2007).

To disclose the functions of NRP, numbers of animal models have been used. According to the primary report saying that NRP1 was involved in angiogenesis, embryo of the transgenic mouse was in danger by NRP1 over-expression with showing such symptoms as excessive angiogenesis, expanded blood vessels, bleeding, and abnormal heart and limbs development (Herzog Y et al., Mech Dev., 2001). In the NRP1 knock-out mouse, embryo was deceased in uterus on the $12.5^{th}$ and $13.5^{th}$ day from the development with showing abnormal yorksac, unusual nerve angiogenesis, blood vessel system disorder, branching deficiency, capillary network deficiency, immature bronchial arches, abnormal dorsal aorta, and cardiovascular disorder including aortic arches (Yuan L et al, Development, 2002). In the NRP2 knock-out mouse, artery and vein were developed normally, but lymph node and microvessel formation was significantly decreased (Yuan L et al, Development, 2002). In the NRP1/NRP2 knock-out mouse, embryo was deceased on the $8.5^{th}$ day from the development with showing avascular yorksac, growth suppression, and more serious vascular disorder such as vascular development deficiency, capillary formation deficiency, and branching deficiency (Eichmann A et al, Int J Dev Biol, 2005).

Matrix metallopeptidase 9 (MMP-9) is involved in outer cell wall matrix degradation not only in normal physiological processes including embryo development, regeneration, and tissue remodeling, etc, not also in disease processes such as arthritis and metastasis. Most MMPs are secreted in the form of inactive proproteins, which are then divided by extracellular proteinases. The enzyme encoded by MMP-9 decomposes collagen IV and V. According to the previous studies using rhesus monkey, the enzyme encoded by MMP-9 was involved in the mobility of hematopoietic progenitor cells originated from bone marrow mediated by IL-8. According to other studies using animals of the rat genus, MMP-9 was involved in tissue remodeling in relation to tumor.

MMP-9 is generated by a specific stimulus in macrophages (Welgus H G et al, J Clin Invest, 1990), eosinophils (Hno I et al, Am J Respir Cell Mol. Biol., 1997), macrophages (Kanbe N, et al., Eur J Immunol, 1999), and dendritic cells (Bartholome E J, J Interferon Cytokine Res, 2001). MMP-9 is a kind of inflammatory molecule that plays a role in maintaining immune response (Renckens R. et al, J Immunol, 2006) and at the same time is involved in the regeneration of damaged tissues. MMP-9 is directly involved in airway inflammation, so MMP-9 expression is increased in sputum. MMP-9 is functioning to make airway thicker (Matsumoto H, et al, Thorax, 2005). There have been numbers of reports saying that MMP-9 is involved in respiratory disease such as asthma, but the exact mechanism thereof has not been disclosed, yet.

The preset inventors have been studied for the development of a novel asthma marker or a therapeutic agent for asthma. As a result, the inventors completed this invention by confirming the followings: Expressions of inflammatory cytokine and NRP1 were increased in cells when *D. pteronissinus* extract known to cause asthma was treated to the cells; NRP1 expression was significantly increased in peripheral blood cells of asthma patient, compared with that in the normal control; MMP-9 mRNA, protein activity, and enzyme activity were all decreased by NRP1 expression or activity inhibitor; and MMP-9 promoter activity was reduced by NRP1 expression or activity inhibitor dose-dependently; which all suggested that NRP1 (neuropilin 1) gene could be effectively used as a marker for the diagnosis of asthma and thereby the said gene marker could be effectively used for the screening of a therapeutic agent for asthma.

REFERENCES

Takagi S, Tsuji T, Amagai T, Takamatsu T, Fujisawa H. Specific cell surface labels in the visual centers of *Xenopus laevis* tadpole identified using monoclonal antibodies. Dev Biol 1987; 122:90-100.

He Z, Tessier-Lavigne M. Neuropilin is a receptor for the axonal chemorepellent. Semaphorin III. Cell 1997; 90:739-751.

Soker S, Takashima S, Miao H Q, Neufeld G, Klagsbrun M. Neuropilin-1 is expressed by endothelial and tumor cells as an isoform specific receptor for vascular endothelial growth factor. Cell 1998; 92:735-745.

Caroline PELLET-MANY, Paul FRANKEL, Haiyan JIA, and Ian ZACHARY. (2008) Neuropilins: structure, function and role in disease (REVIEW ARTICLE).

Bielenberg, D. R., Pettaway, C. A., Takashima, S, and Klagsbrun, M. (2006) Neuropilins in neoplasms: expression, regulation, and function. Exp. Cell Res. 312, 584-593.

Soker, S., Takashima, S., Miao, H. Q., Neufeld, G. and Klagsbrun, M. (1998) Neuropilin-1 is expressed by endothelial and tumor cells as an isoform-specific receptor for vascular endothelial growth factor. Cell 92, 735-745.

Ellis, L. M. (2006) The role of neuropilins in cancer. Mol. Cancer. Ther. 5, 1099-1107.

Bachelder, R. E., Crago, A., Chung, J., Wendt, M. A., Shaw, L. M., Robinson, G. and Mercurio, A. M. (2001) Vascular endothelial growth factor is an autocrine survival factor for neuropilin-expressing breast carcinoma cells. Cancer Res. 61, 5736-5740.

Chabbert-de Ponnat, I., Buffard, V., Leroy, K., Bagot, M., Bensussan, A., Wolkenstein, P. and Marie-Cardine, A. (2006) Antiproliferative effect of semaphorin 3F on human melanoma cell lines. J. Invest. Dermatol. 126, 2343-2345.

Miao, H. Q., Lee, P., Lin, H., Soker, S, and Klagsbrun, M. (2000) Neuropilin-1 expression by tumor cells promotes tumor angiogenesis and progression. FASEB J. 14, 2532-2539.

Fujisawa, H., Takagi, S, and Hirata, T. (1995) Growth-associated expression of a membrane protein, neuropilin, in *Xenopus* optic nerve fibers. Dev. Neurosci. 17, 343-349.

Matthies, A. M., Low, Q. E., Lingen, M. W. and DiPietro, L. A. (2002) Neuropilin-1 participates in wound angiogenesis. Am. J. Pathol. 160, 289-296.

Elena Gerettil, Michael Klagsbrun Targets for Anti-Angiogenesis Therapies Cell Adhesion & Migration 2007; Vol. 1 Issue 2.

Herzog Y, Kalcheim C, Kahane N, Reshef R, Neufeld G. Differential expression of neuropilin-1 and neuropilin-2 in arteries and veins. Mech Dev 2001; 109:115-9.

Yuan L, Moyon D, Pardanaud L, Breant C, Karkkainen M J, Alitalo K, Eichmann A. Abnormal lymphatic vessel development in neuropilin 2 mutant mice. Development 2002; 129:4797-4806.

Eichmann A, Yuan L, Moyon D, Lenoble F, Pardanaud L, Breant C. Vascular development: From precursor cells to branched arterial and venous networks. Int J Dev Biol 2005; 49:259-267.

SUMMARY OF THE INVENTION

It is an object of the present invention to provide a kit for the diagnosis of asthma using NRP1 (neuropilin 1) gene.

It is another object of the present invention to provide a method for the diagnosis of asthma using NRP1 (neuropilin 1) gene.

It is further an object of the present invention to provide a method for screening a therapeutic agent for asthma using NRP1.

In addition, it is also an object of the present invention to provide a pharmaceutical composition for the treatment of asthma comprising NRP1 gene expression or activity inhibitor as an active ingredient.

To achieve the above objects, the present invention provides a DNA microarray for the diagnosis of asthma comprising NRP1 (neuropilin 1) gene or its complementary strand molecule.

The present invention also provides a kit for the diagnosis of asthma comprising the DNA microarray for the diagnosis of asthma containing NRP1 (neuropilin 1) gene or its complementary strand molecule.

The present invention further provides a kit for the diagnosis of asthma comprising the primer set composed of the forward primer and the reverse primer which are complementary to NRP1 gene and at the same time capable of amplifying the said NRP1 gene.

The present invention also provides a protein detection method to provide information for asthma diagnosis comprising the following steps:

1) measuring NRP1 expression in the sample originated from the test subject used as the experimental group;
2) comparing the NRP1 expression level measured in step 1) with the NRP1 expression level in the sample originated from the normal subject used as the control group; and
3) diagnosing the test subject with high risk of asthma when the NRP1 expression is higher than that of the control.

The present invention also provides a method for screening a therapeutic agent for asthma comprising the following steps:

1) treating test compounds or compositions to the cell line expressing NRP1 or both NPR1 and MMP-9;
2) measuring NRP1 or both NRP1 and MMP-9 expressions in the cell line treated with the test compounds or compositions of step 1); and
3) selecting test compounds or compositions demonstrating down-regulation of NRP1 or both NRP1 and MMP-9 expressions in the cell line of step 2), compared with the control cell line not treated with any of them.

The present invention also provides a method for screening a therapeutic agent for asthma comprising the following steps:

1) treating test compounds or compositions to the kit for the diagnosis of asthma comprising the said DNA microarray or to the kit for the diagnosis of asthma comprising the primer set composed of the forward primer and the reverse primer which are complementary to NRP1 gene and at the same time capable of amplifying the said gene;
2) measuring NRP1 expression in the kit treated above in step 1); and
3) selecting test compounds or compositions demonstrating down-regulation of NRP1 by comparing the expression of NRP1 with that of the control.

The present invention also provides a pharmaceutical composition for the treatment of asthma comprising NRP1 gene expression or activity inhibitor as an active ingredient.

The present invention also provides a method for relieving or treating asthma comprising the step of administering a pharmaceutically effective dose of NRP1 gene expression or activity inhibitor to a subject.

In addition, the present invention provides NRP1 gene expression or activity inhibitor to be used as a pharmaceutical composition for the treatment of asthma.

Advantageous Effect

As explained hereinbefore, the NRP1 gene of the present invention is up-regulated by the extract of *D. pteronissinus* known to cause asthma and the expression thereof is observed in peripheral blood cells of asthma patients more significantly than in the normal subject. And, asthma related MMP-9 expression, enzyme activity, and promoter activity can be inhibited by the suppression of NRP1 expression. Therefore, NRP1 (neuropilin 1) gene can be effectively used for the kit for the diagnosis of asthma and for the screening of a therapeutic agent for asthma using the same.

BRIEF DESCRIPTION OF THE DRAWINGS

The application of the preferred embodiments of the present invention is best understood with reference to the accompanying drawings, wherein:

FIG. 1A is a graph confirming the cytokine IL6 mRNA expression in THP1 cell line after the treatment of *D. pteronissinus* extract;
LPS: Lipopolysaccharides;
*: $p<0.05$;
***: $p<0.001$;

FIG. 1B is a graph confirming the cytokine IL8 mRNA expression in THP1 cell line after the treatment of *D. pteronissinus* extract;
LPS: Lipopolysaccharides;
**: $p<0.01$;
***: $p<0.001$;

FIG. 1C is a graph confirming the cytokine MCP1 mRNA expression in THP1 cell line after the treatment of *D. pteronissinus* extract;
LPS: Lipopolysaccharides;
***: $p<0.001$;

FIG. 1D is a graph confirming the cytokine IL8 mRNA expression in THP1 cell line after the treatment of *D. pteronissinus* extract;
**: $p<0.01$;
***: $p<0.001$; and
LPS: Lipopolysaccharides.

FIG. 2A is a graph illustrating the decrease of NRP1 mRNA expression in THP1 cell line after the treatment of *D. pteronissinus* extract and NRP1 siRNA capable of inhibiting NRP1 gene expression;
si-control: control siRNA;
si-NRP1: NRP1 siRNA;
LPS: Lipopolysaccharides;
***: $p<0.001$;

FIG. 2B is a graph illustrating the decrease of the cytokine IL6 mRNA expression in THP1 cell line after the treatment of *D. pteronissinus* extract and NRP1 siRNA;
si-control: control siRNA;
si-NRP1: NRP1 siRNA;
LPS: Lipopolysaccharides;
*: $p<0.05$;
**: $p<0.01$;

FIG. 2C is a graph illustrating the decrease of the cytokine IL8 mRNA expression in THP1 cell line after the treatment of *D. pteronissinus* extract and NRP1 siRNA;
si-control: control siRNA;
si-NRP1: NRP1 siRNA;
LPS: Lipopolysaccharides;
**: $p<0.01$;
***: $p<0.001$;

FIG. 2D is a graph illustrating the decrease of the cytokine MCP1 mRNA expression in THP1 cell line after the treatment of *D. pteronissinus* extract and NRP1 siRNA;
si-control: control siRNA;
si-NRP1: NRP1 siRNA;
LPS: Lipopolysaccharides; and
***: $p<0.001$.

FIG. 3A is a graph illustrating the comparison of NRP1 mRNA expression in peripheral blood cells between the normal control group and asthma patient group;
**: $p<0.01$;

FIG. 3B is a graph illustrating the comparison of NRP1 mRNA expression in peripheral blood cells between the not-administered asthma patient group and the administered asthma patient group; and

**: p<0.01.

Figure 4:
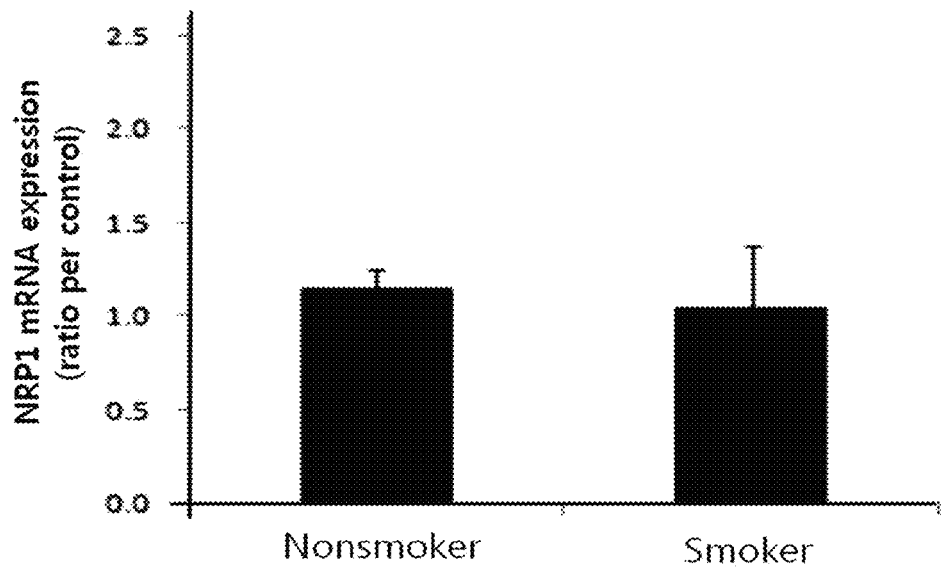
Figure 4:
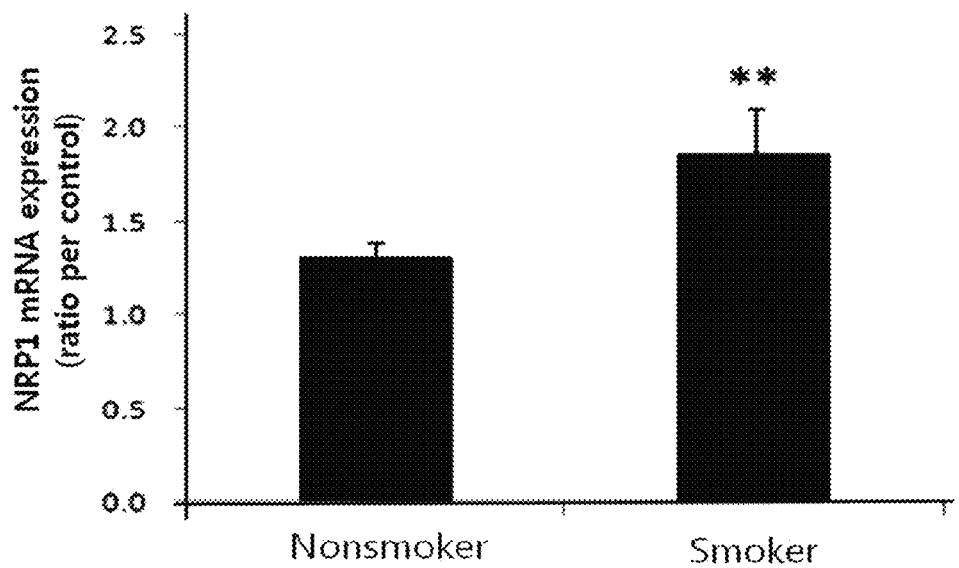

FIG. 4 is a set of graphs illustrating the NRP1 expression patterns of both the normal control group and asthma patient group according to smoking behavior:

FIG. 4A is a graph illustrating the NRP1 mRNA expression patterns in peripheral blood cells of the normal control group according to smoking or non-smoking;

FIG. 4B is a graph illustrating the NRP1 mRNA expression patterns in peripheral blood cells of the asthma patient group according to smoking or non-smoking; and

**: p<0.01.

Figure 5:
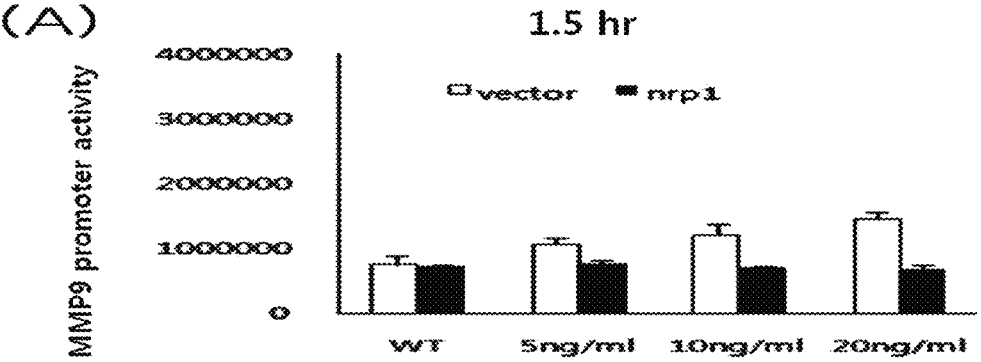
Figure 5:
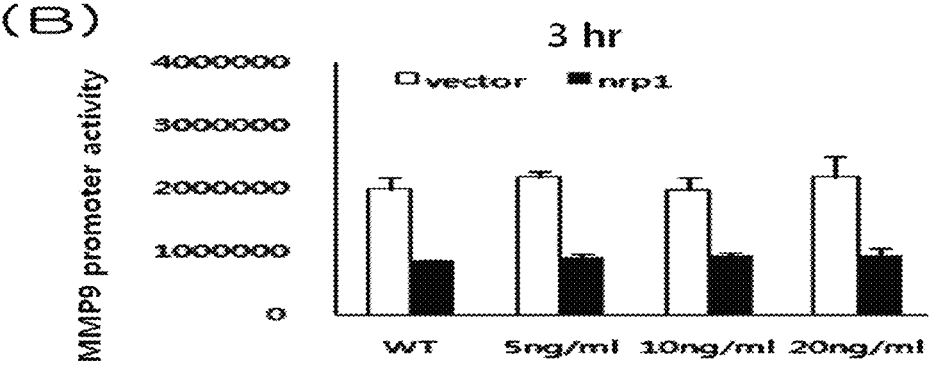
Figure 5:
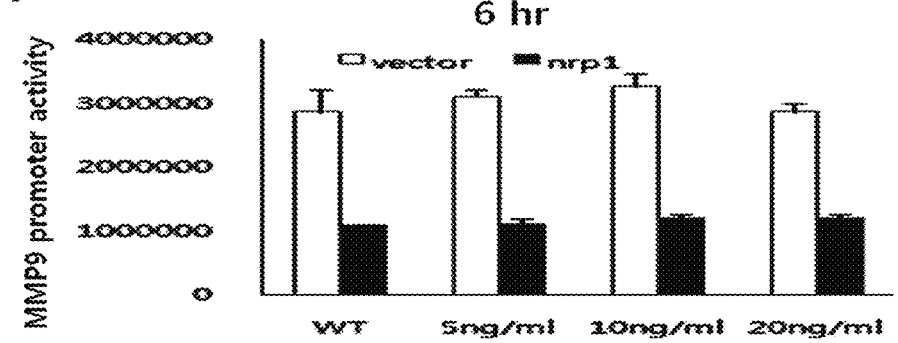

FIG. 5 is a set of graphs illustrating the involvement of MMP-9 and NRP1 in asthma:

FIG. 5A is a graph illustrating the MMP-9 promoter activity over the concentrations of NRP1 shRNA measured in RAW 264.7 cell line harboring pGL4.14-pMMP-9(−670/+3) vector enabling the measurement of MMP-9 promoter activity after the treatment of NRP1-shRNA for 1.5 h;

WT: non-treated RAW 264.7 cell line;
vector: control shRNA;
nrp1: NRP1 shRNA;

FIG. 5B is a graph illustrating the MMP-9 promoter activity over the concentrations of NRP1 shRNA measured in RAW 264.7 cell line harboring pGL4.14-pMMP-9(−670/+3) vector enabling the measurement of MMP-9 promoter activity after the treatment of NRP1-shRNA for 3 h;

WT: non-treated RAW 264.7 cell line;
vector: control shRNA;
nrp1: NRP1 shRNA;

FIG. 5C is a graph illustrating the MMP-9 promoter activity over the concentrations of NRP1 shRNA measured in RAW 264.7 cell line harboring pGL4.14-pMMP-9(−670/+3) vector enabling the measurement of MMP-9 promoter activity after the treatment of NRP1-shRNA for 6 h;

WT: non-treated RAW 264.7 cell line;
vector: control shRNA; and
nrp1: NRP1 shRNA.

Figure 6:
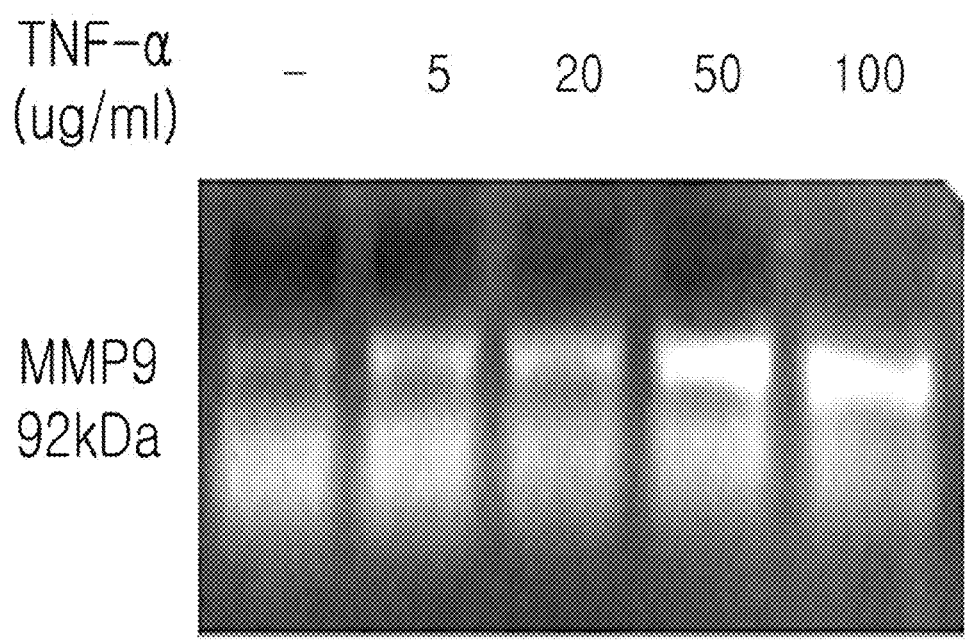

FIG. 6 is a diagram illustrating the result of gelatin zymography showing the increase of MMP-9 enzyme activity over the concentrations of INF-α in HT1080 cell line after the treatment of INF-α for 24 h.

Figure 7:
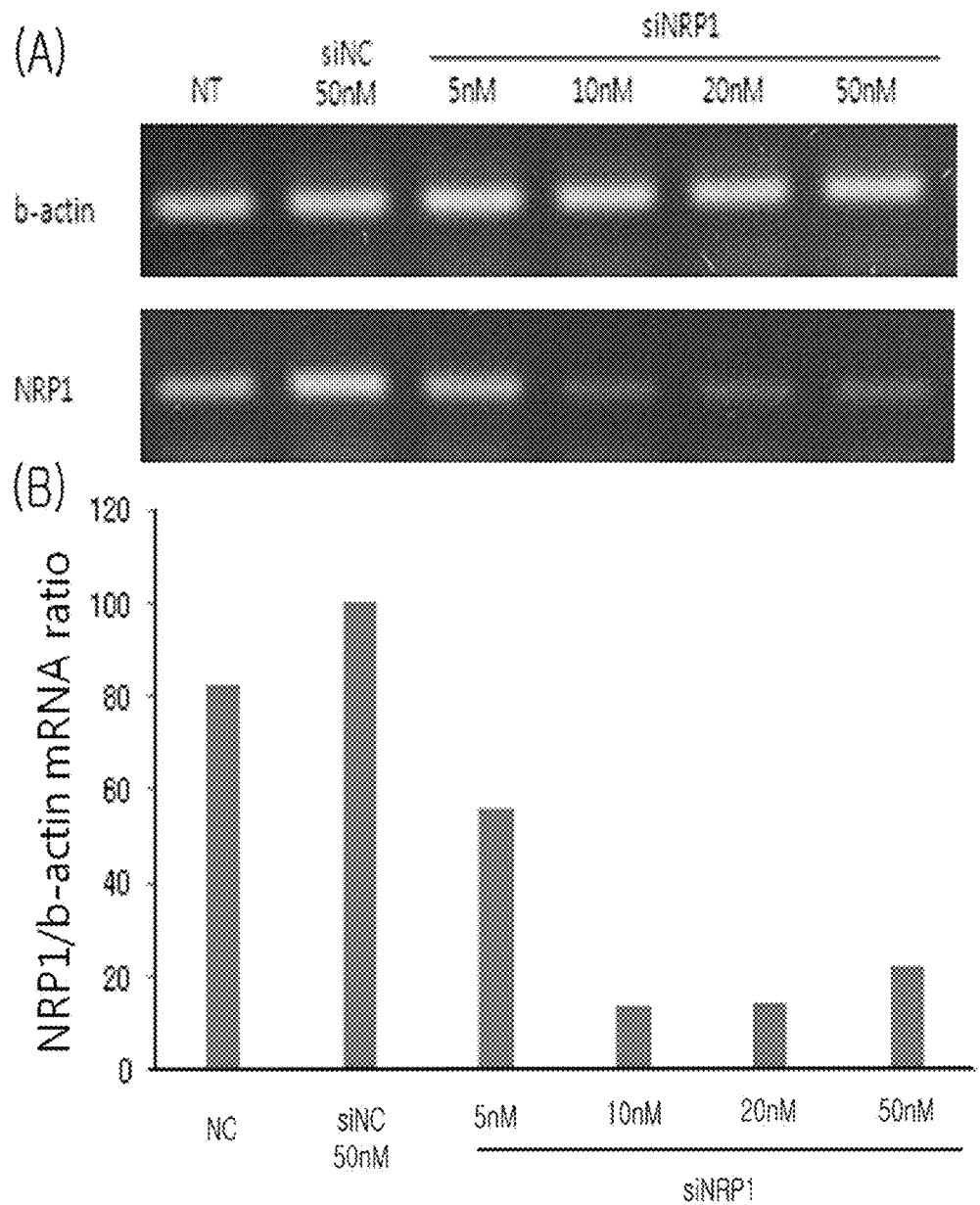

FIG. 7 is a set of a diagram and a graph illustrating the effect of NRP1 siRNA in HT1080 cell line:

FIG. 7A is a diagram illustrating the NRP1 mRNA expression over the concentrations of NRP1 siRNA in HT1080 cell line;

NT: non-treated HT1080 cell line;
siNC: control siRNA;
siNRP1: NRP1 siRNA;

FIG. 7B is a graph illustrating the NRP1 mRNA expression over the concentrations of NRP1 siRNA in HT1080 cell line, which was quantified based on the amount of beta-actin mRNA;

αNT: non-treated HT1080 cell line;
siNC: control siRNA; and
siNRP1: NRP1 siRNA.

Figure 8:
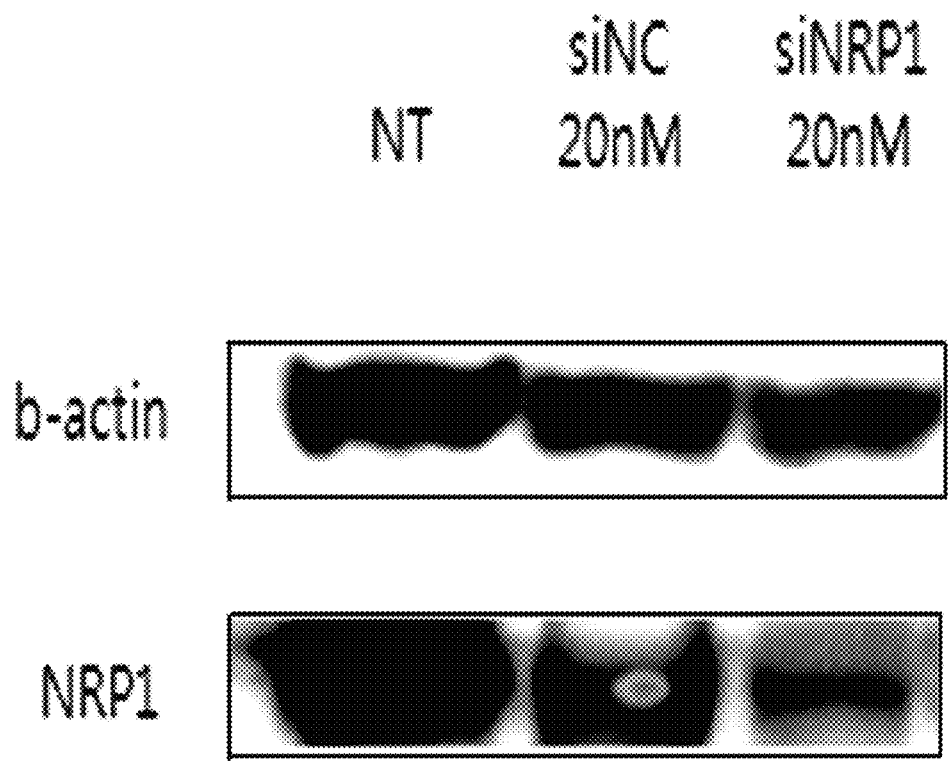

FIG. 8 is a diagram illustrating the NRP1 protein expression in HT1080 cell line over the treatment of NRP1 siRNA:

NT: non-treated HT1080 cell line;
siNC: control siRNA; and
siNRP1: NRP1 siRNA.

Figure 9:
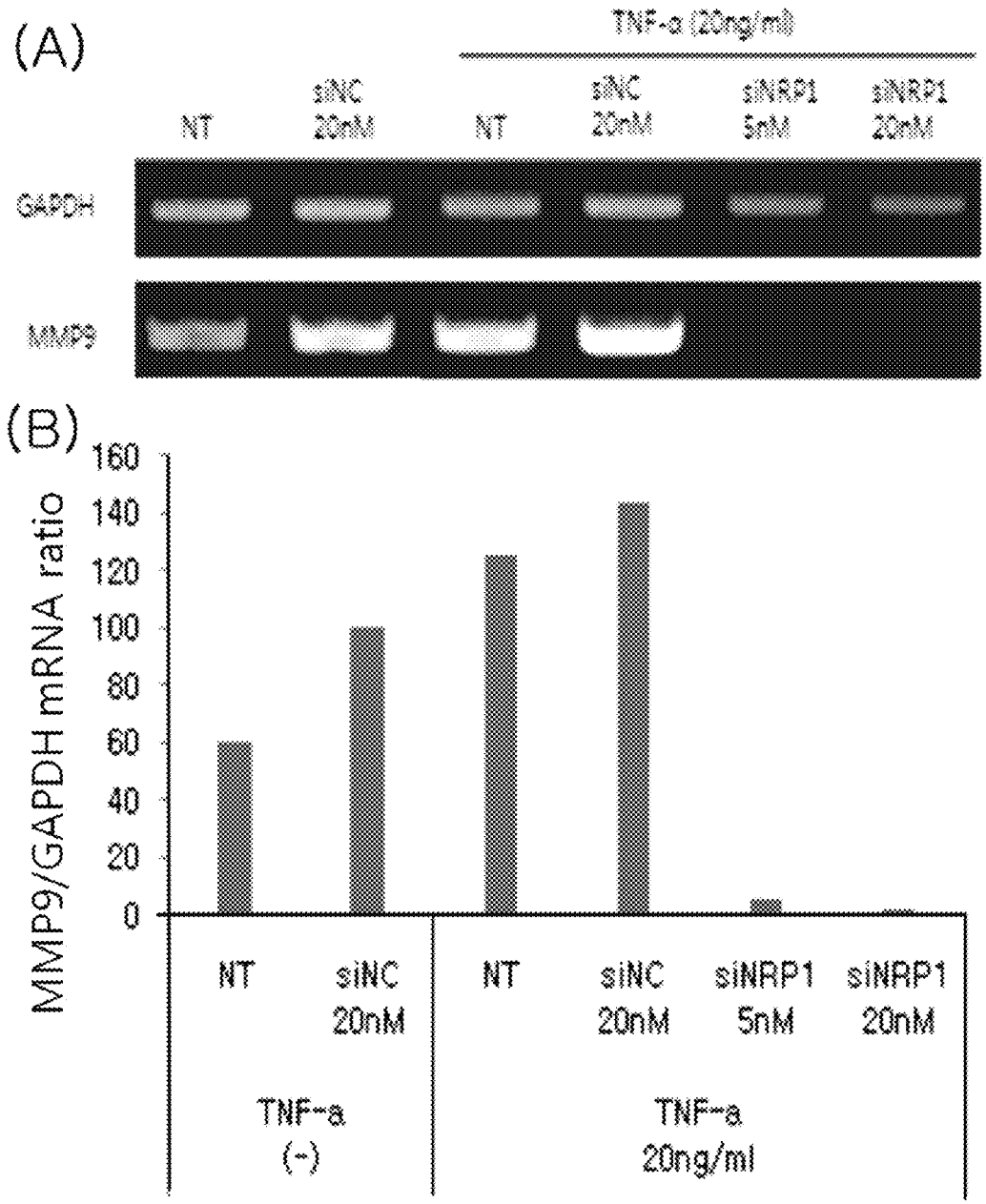

FIG. 9 is a set of a diagram and a graph illustrating the decrease of MMP-9 expression after the suppression of NRP1 expression:

FIG. 9A is a diagram illustrating that the MMP-9 mRNA expression increased by TNF-α was reduced by NRP1 siRNA;

FIG. 9B is a graph illustrating the decrease of MMP-9 mRNA expression by NRP1 siRNA which had been up-regulated by TNF-α, which was quantified based on the amount of GAPDH expression;

NT: non-treated HT1080 cell line;
siNC: control siRNA; and
siNRP1: NRP1의 siRNA.

Figure 10:
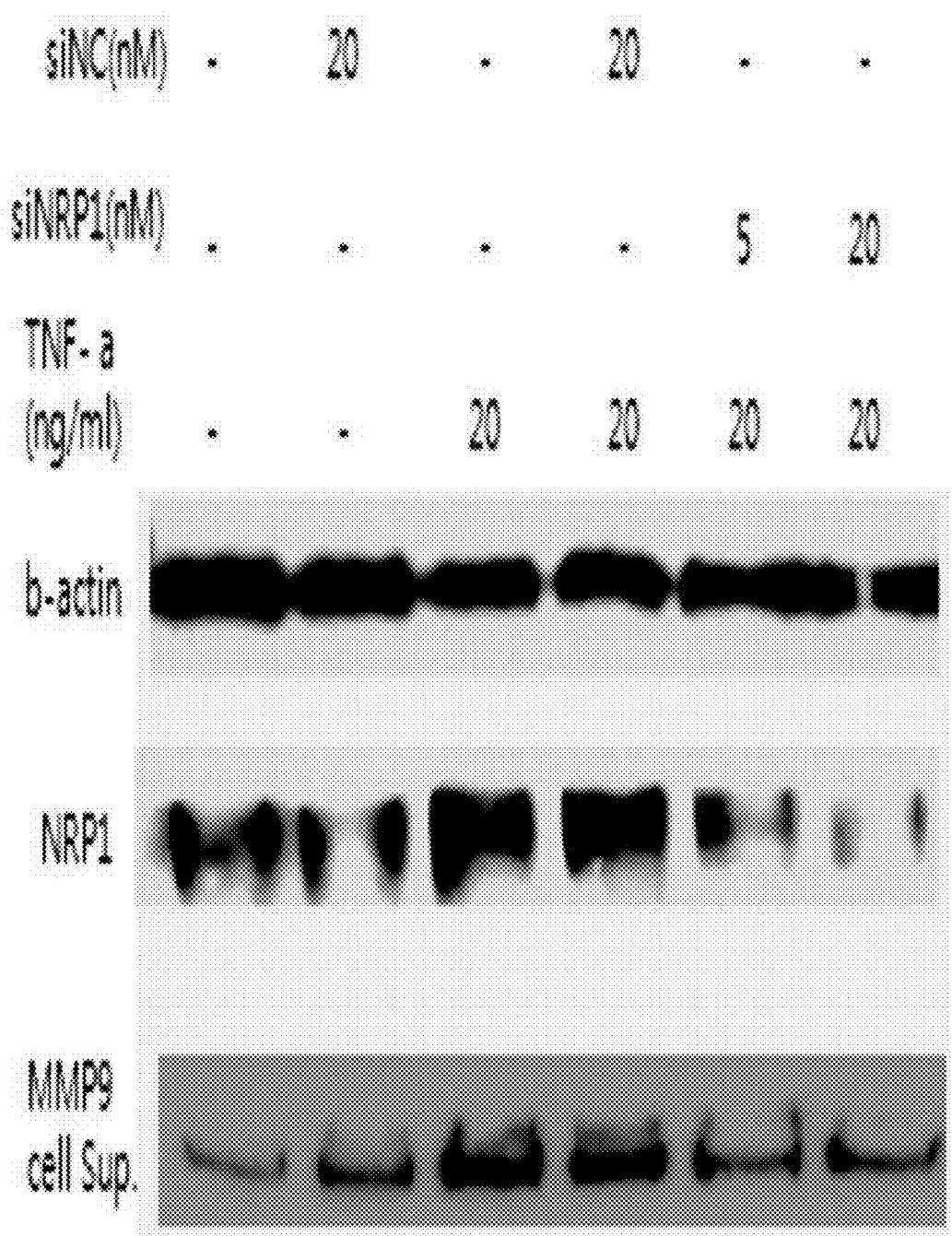

FIG. 10 is a diagram illustrating the decrease of MMP-9 expression by NRP1 siRNA which had been up-regulated by TNF-α, which was confirmed by Western blotting:

siNC: control siRNA; and
siNRP1: NRP1 siRNA.

Figure 11:
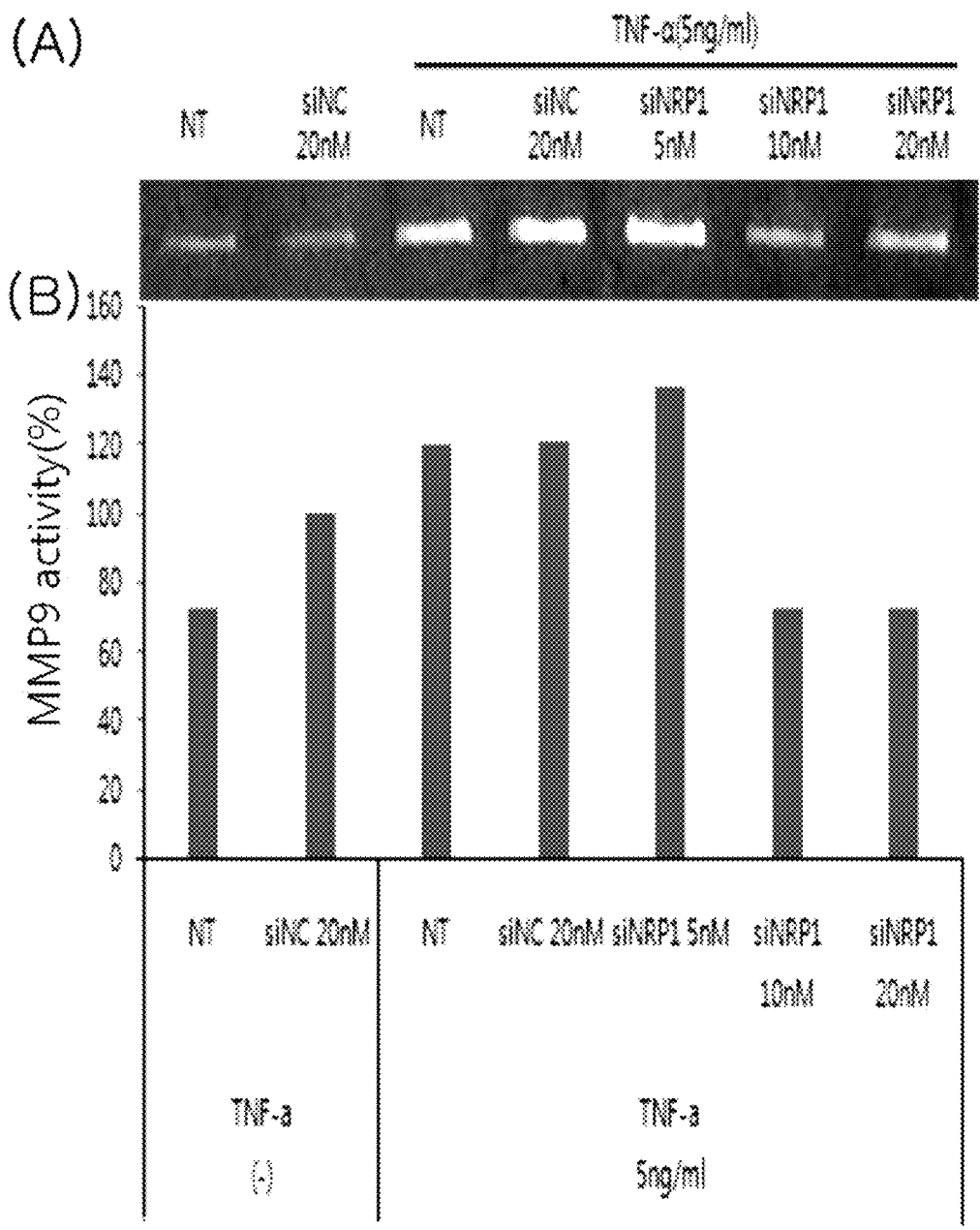

FIG. 11 is a set of a diagram and a graph illustrating that MMP-9 enzyme activity induced by TNF-α was reduced by the treatment of NRP1 siRNA dose-dependently:

FIG. 11A is a diagram illustrating the MMP-9 enzyme activity in HT1080 cell line treated with TNF-α for 24 h and NRP1 siRNA at different concentrations, confirmed by gelatin zymography;

NT: non-treated HT1080 cell line;
siNC: control siRNA;
siNRP1: NRP1 siRNA;

FIG. 11B is a graph illustrating the MMP-9 enzyme activity in HT1080 cell line treated with TNF-α for 24 h and NRP1 siRNA at different concentrations, quantified by densitometry;

NT: non-treated HT1080 cell line;
siNC: control siRNA; and
siNRP1: NRP1의 siRNA.

Figure 12:
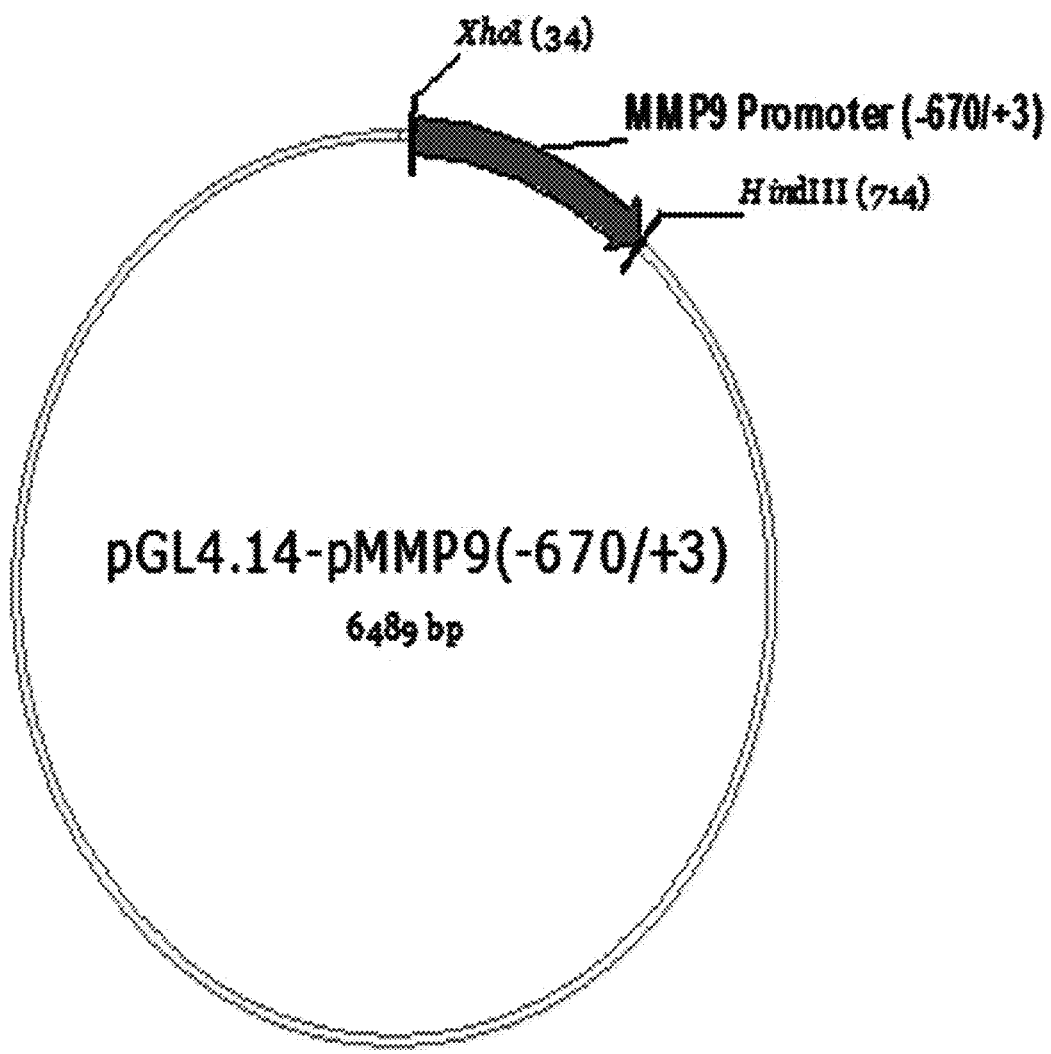

FIG. 12 is a diagram illustrating the pGL4.4-pMMP-9(−670/+3) vector used for luciferase assay to measure MMP-9 promoter activity.

Figure 13:
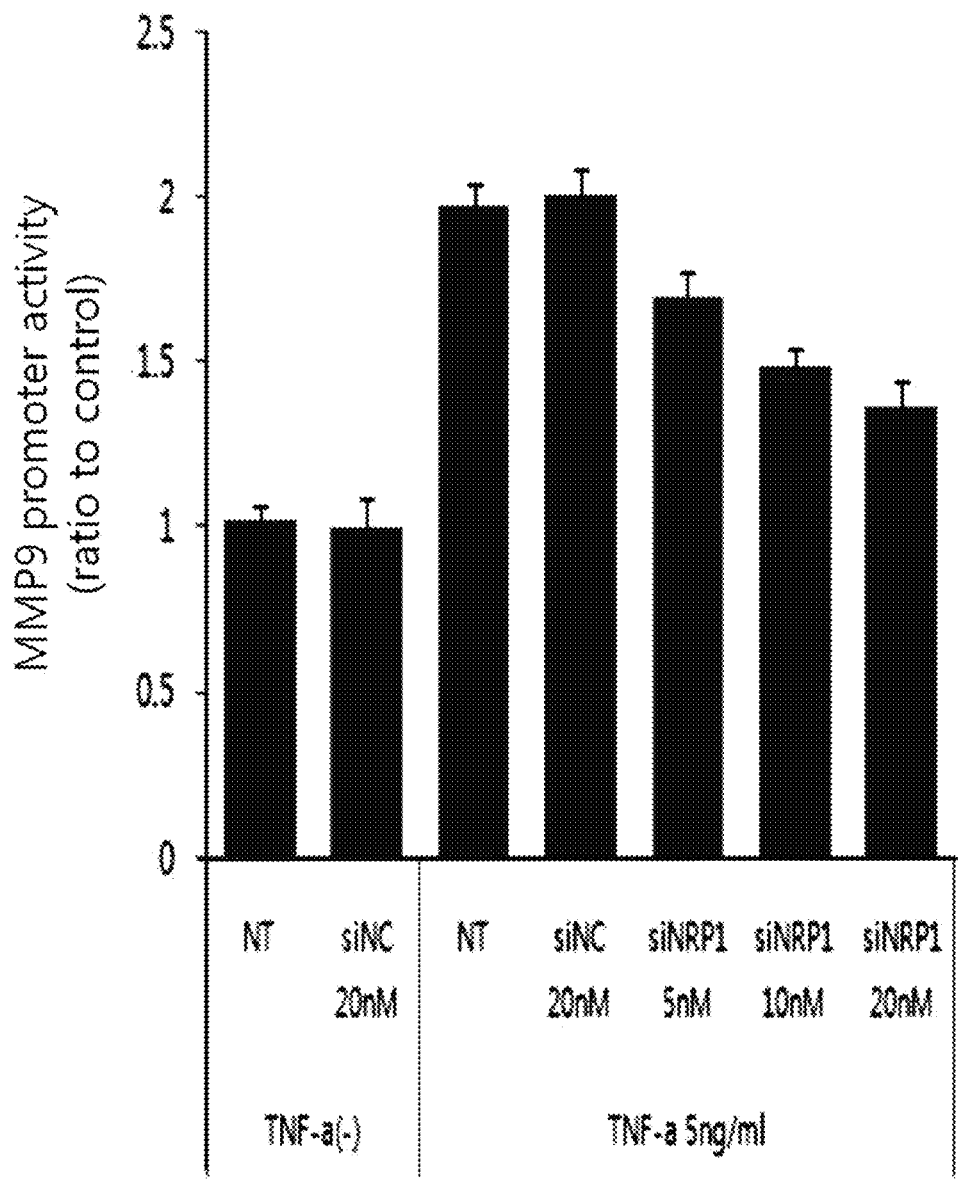

FIG. 13 is a graph illustrating that MMP-9 promoter activity once increased in HT1080 cell line harboring pGL4.4-pMMP-9 vector by the treatment of TNF-α for 24 h was reduced by NRP1 siRNA dose-dependently, confirmed by luciferase assay:

NT: non-treated HT1080 cell line;
siNC: control siRNA; and
siNRP1: NRP1 siRNA.

DESCRIPTION OF THE PREFERRED EMBODIMENTS

Hereinafter, the present invention is described in detail.

The present invention provides a DNA microarray for the diagnosis of asthma comprising the oligonucleotide that is a fragment of NRP1 (neuropilin 1) gene comprising the nucleic acid sequence of the same or its complementary strand molecule.

In the DNA microarray for the diagnosis of asthma, the NRP1 gene herein preferably has the nucleotide sequence represented by SEQ. ID. NO: 1, but not always limited thereto.

In a preferred embodiment of the present invention, the present inventors treated the extract of *D. pteronyssinus* known to cause asthma to THP1 cells originated from acute monocytic leukemia at different concentrations, followed by investigation of the expressions of IL6, IL8, and MCP1, the inflammatory cytokines, and the expression of mRNA. For the positive control, lipopolysacchardes (LPS) known to induce inflammatory cytokines was treated. As a result, inflammatory cytokines were up-regulated as the concentration of *D. pteronyssinus* extract increased. This increase was similar to the increase of inflammatory cytokines under the treatment of LPS, the positive control. In addition, NRP1 mRNA was also increased by *D. pteronyssinus* extract (see FIG. 1).

Figure 2:
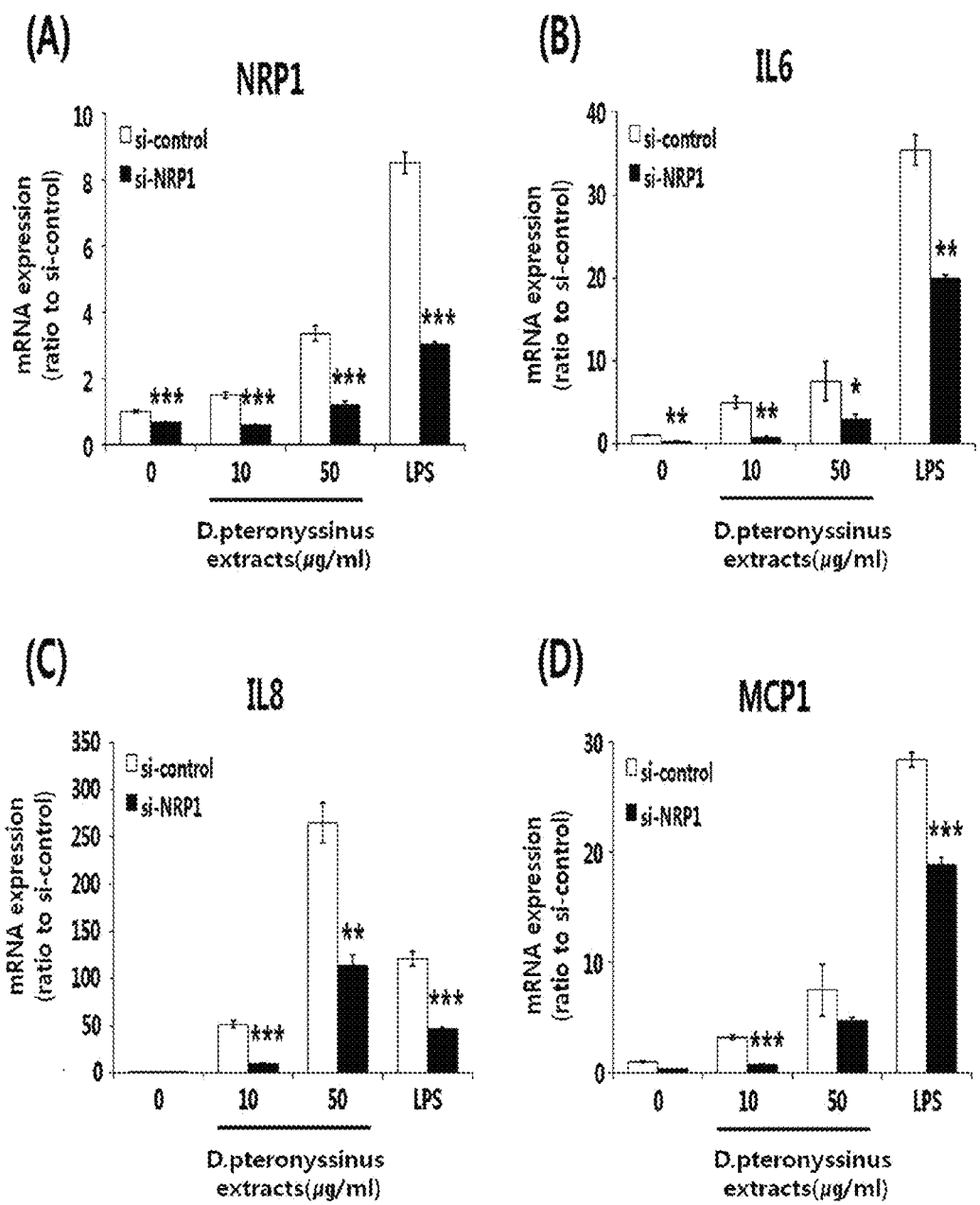
FIG. 2 is a set of graphs illustrating the decrease of the inflammatory cytokine that has been increased by *D. pteronissinus* extract by the treatment of NRP1 siRNA.

In a preferred embodiment of the present invention, THP1 cells were treated with *D. pteronyssinus* extract and NRP1 siRNA. Particularly, to investigate whether or not NRP1 siRNA inhibited NRP1 expression effectively, THP1 cells were first treated with *D. pteronyssinus* extract and NRP1 siRNA. Then, the expression of NRP1 was observed. As a result, in the group treated with NRP1 siRNA, the expression of NRP1 mRNA was significantly reduced, compared with the control group treated with the control siRNA, suggesting that NRP1 siRNA was effectively functioning. In the meantime, it was also observed that the expressions of inflammatory cytokines such as IL6, IL8, and MCP1, which were increased by the treatment of *D. pteronyssinus* extract, were significantly reduced as well, compared with the control group treated with the control siRNA (see FIG. 2).

Figure 3:
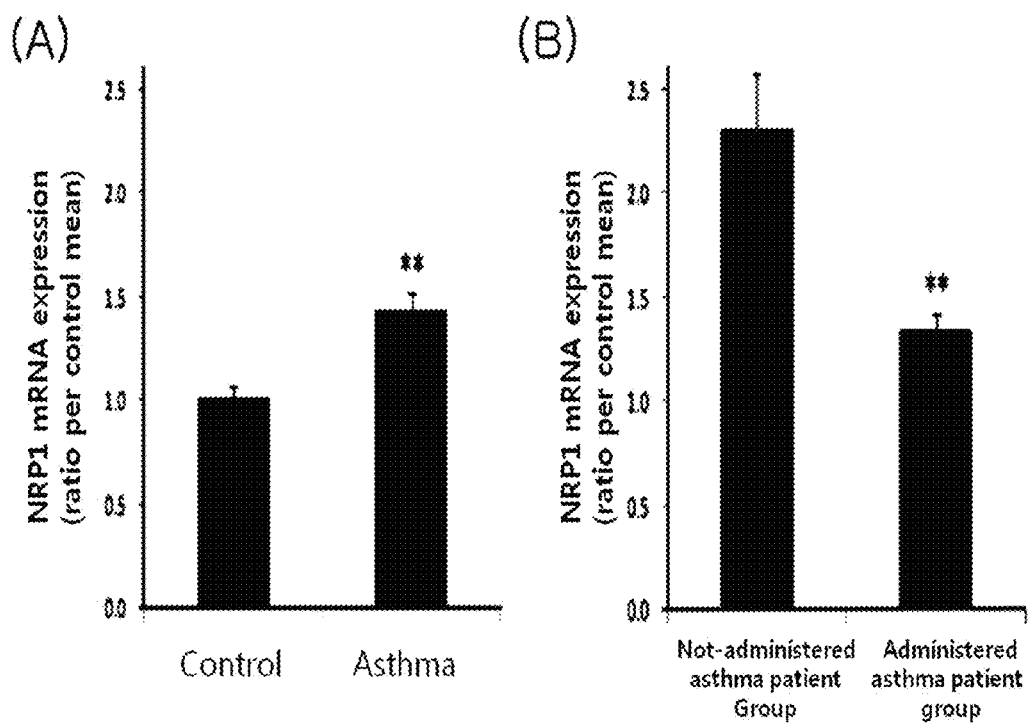
FIG. 3 is a set of graphs illustrating the comparison of NRP1 expression in peripheral blood cells between the normal control group and asthma patient group.

In a preferred embodiment of the present invention, the expression of NRP1 mRNA in peripheral blood cells was compared between normal people and asthma patients. As a result, NRP1 expression was significantly increased in peripheral blood cells of asthma patients, compared with the normal control. In the meantime, NRP1 expression was significantly reduced in the group treated with asthma drug (see FIG. 3). The present inventors also investigated whether or not NRP1 expression in peripheral blood cells could be affected by smoking in both normal people and asthma patients. As a result, when asthma patients were smokers, NRP1 expression was significantly increased, compared with non-smoking asthma patients (see FIG. 4). The present inventors additionally studied how NRP1 expression was affected by other diseases such as tuberculosis, allergic rhinitis, atopic dermatitis, and urticaria. As a result, when asthma patients had atopic dermatitis, NRP1 expression was increased (see Tables 1 and 2).

In a preferred embodiment of the present invention, NRP1 shRNA was treated to RAW 264.7 cell line harboring pGL4.14-pMMP-9 (-630/+3) vector capable of measuring MMP-9 promoter activity at different concentrations, followed by measurement of MMP-9 promoter activity. The increase of MMP-9 expression has been regarded as an important reason causing airway remodeling, one of the major pathogenic features of chronic asthma. NRP1 shRNA was treated to RAW 264.7 cell line at different concentrations at a regular time interval, followed by luciferase assay. As a result, as the concentration of NRP1 shRNA increased and as the treatment time increased from 1.5 h to 6 h, MMP-9 expression was decreased (see FIG. 5). In the meantime, NRP1 siRNA was also treated to HT1090 cells at different concentrations and then MMP-9 enzyme activity changes were investigated by zymography. As a result, MMP-9 activity was decreased by the treatment of NRP1 siRNA dose-dependently (see FIG. 6).

In a preferred embodiment of the present invention, to investigate NRP1 siRNA effect on HT1080 cells, NRP1 siRNA was treated thereto at the concentrations of 5, 10, 20, and 50 nM, followed by observation of NRP1 mRNA expression patterns. As a result, according to the treatment of NRP1 siRNA, NRP1 expression was significantly reduced, compared with the negative control treated with the control siRNA. NRP1 expression was most effectively inhibited when NRP1 siRNA was treated at the concentrations of 10 nM and 20 nM (see FIG. 7). To investigate whether or not NRP1 siRNA could inhibit NRP1 protein expression likewise, 20 nM of NRP1 siRNA, confirmed to inhibit NRP1 expression effectively, was treated to HT1080 cells, followed by Western blotting to measure NRP1 protein expression. As a result, NRP1 protein expression was effectively inhibited in the group treated with NRP1 siRNA, compared with the group treated with the control siRNA (see FIG. 8).

In a preferred embodiment of the present invention, to confirm the asthma treatment effect of NRP1 siRNA, HT1080 cells were treated with NRP1 siRNA at the concentrations of 5 and 20 nM, followed by TNF-α treatment. The present inventors then observed whether or not NRP1 siRNA could inhibit MMP and NRP1 expressions increased by TNF-α. As a result, TNF-α treatment increased MMP-9 expression, but NRP1 siRNA treatment inhibited MMP-9 expression dose-dependently (see FIG. 9). To investigate if NRP1 siRNA could reduce MMP-9 and NRP1 expressions increased by TNF-α at protein level, the present inventors treated HT1080 cells with NRP1 siRNA and TNF-α under the same condition as described in FIG. 9. Then, Western blotting was performed to measure MMP-9 and NRP1 protein expressions. As a result, NRP1 and MMP-9 protein expressions were increased by TNF-α, but reduced by NRP1 siRNA dose-dependently (see FIG. 10). In addition, the present inventors tried to investigate whether or not MMP-9 enzyme activity increased by TNF-α could be reduced by NRP1 siRNA. To do so, HT1080 cells were treated with NRP1 siRNA and TNF-α, followed by measurement of MMP-9 enzyme activity by using gelatin zymography. As a result, as shown in FIG. 9-FIG. 13, MMP-9 enzyme activity increased by TNF-α was reduced by NRP1 siRNA dose-dependently (see FIG. 11).

To observe MMP-9 promoter activity changes by NRP1 siRNA, pGL4.14-pMMP(-670/+3) vector containing MMP-9 promoter region was constructed (see FIG. 12). HT1080 cells harboring the said pGL4.14-pMMP(-670/+3) vector were treated with NRP1 siRNA at the concentrations of 5, 10, and 20 nM, followed by luciferase assay. As a result, MMP-9 promoter activity increased by TNF-α was reduced NRP1 siRNA dose-dependently (see FIG. 13).

Therefore, the relation between NRP1 and asthma has been disclosed by preferred embodiments of the present invention. More particularly, the present invention confirmed that MMP-9 expression and function were inhibited by NRP1 expression or activity inhibitor, suggesting that NRP1 (neuropilin 1) could be effectively used as a target for the development of a marker for the diagnosis of asthma or a therapeutic agent for asthma.

The present invention also provides a kit for the diagnosis of asthma comprising the DNA microarray for the diagnosis of asthma containing the oligonucleotide which is a fragment of NRP1 (neuropilin 1) gene nucleic acid sequence or its complementary strand molecule.

In a preferred embodiment of the present invention, it was observed that NRP1 gene expression was increased by an asthma inducing factor and the expression was specifically up-regulated in peripheral blood cells of asthma patients, compared with that of the normal subject. In addition, asthma related MMP-9 gene expression and function were also reduced by NRP1 expression or activity inhibitor, suggesting that the DNA microarray comprising NRP1 gene could be effectively used as a kit for the diagnosis of asthma.

The present invention also provides a kit for the diagnosis of asthma comprising the primer set composed of the forward primer and the reverse primer which are complementary to NRP1 gene and at the same time capable of amplifying the said NRP1 gene.

The primer set herein is preferably composed of the forward primer having the nucleotide sequence represented by SEQ. ID. NO: 2 (5'-CCACAGTGGAACAGGTGATG-3') and the reverse primer having the nucleotide sequence represented by SEQ. ID. NO: 3 (5'-GCACGTGATTGTCATGT-TCC-3'), but not always limited thereto.

When NRP1 specific primer is used for PCR amplification for the detection of NRP1, reagents for PCR such as buffer, DNA polymerase [for example, thermostable DNA polymerase obtained from Thermus aquaticus (Taq), Thermus thermophilus (Tth), Thermus filiformis, Thermis flavus, Thermococcus literalis, or Pyrococcus furiosus (Pfu)], DNA polymerase cofactor, and dNTPs can be selectively included. The kit of the present invention can be constructed as multiple packages or compartments containing the above-mentioned reagents.

In a preferred embodiment of the present invention, NRP1 gene was particularly up-regulated in peripheral blood cells of asthma patients, compared with normal subject. The expression was increased by the extract of D. pteronyssinus known to cause asthma. In addition, MMP-9 expression and function, known as an important factor developing asthma, were also reduced by NRP1 expression or activity inhibitor. Therefore, it was confirmed that the primer set composed of the forward primer and the reverse primer complementary to NRP1 gene and able to amplify the gene could be effectively used for the diagnosis of asthma.

The present invention also provides a protein detection method to provide information for asthma diagnosis comprising the following steps:

1) measuring NRP1 expression in the sample originated from the test subject used as the experimental group;

2) comparing the NRP1 expression level measured in step 1) with the NRP1 expression level in the sample originated from the normal subject used as the control group; and 3) diagnosing the test subject with high risk of asthma when the NRP1 expression is higher than that of the control.

In the protein detection method to provide information for asthma diagnosis, the sample can be preferably selected from the group consisting of blood, plasma, serum, urine, tear, saliva, sputum, nasal secretion, bronchial secretion, bronchial washing fluid, lung secretion, and bronchoalveolar lavage fluid, but not always limited thereto. In the protein detection method to provide information for asthma diagnosis, the NRP1 expression of step 1) is detected by the method preferably selected from the group consisting of Western blotting, enzyme-linked immunosorbent assay (ELISA), immunohistochemical staining, immunoprecipitation, and immunofluorescence, but not always limited thereto.

In the zymography performed in this invention, NRP1 expression was increased in peripheral blood cells of asthma patients by TNF-α and the extract of D. pteronyssinus known to cause asthma. In the meantime, MMP-9 expression known to be involved in asthma development was inhibited by NRP1 expression or activity inhibitor. Therefore, to provide information necessary for asthma diagnosis, NRP1 expression can be a useful index for the detection of protein to evaluate the risk of asthma, which is NRP1 expression can be compared between the samples originated from the test subject and the normal control to determine the risk of asthma.

The present invention also provides a method for screening a therapeutic agent for asthma comprising the following steps:

1) treating test compounds or compositions to the cell line expressing NRP1 or both NPR1 and MMP-9.

2) measuring NRP1 or both NRP1 and MMP-9 expressions in the cell line treated with the test compounds or compositions of step 1); and 3) selecting test compounds or compositions demonstrating down-regulation of NRP1 or both NRP1 and MMP-9 expressions in the cell line of step 2), compared with the control cell line not treated with any of them.

In the zymography performed in this invention, NRP1 expression was increased in peripheral blood cells of asthma patients by TNF-α and the extract of D. pteronyssinus known to cause asthma, but MMP-9 expression and function known to be involved in asthma development were inhibited by NRP1 expression or activity inhibitor, suggesting that NRP1 gene could be effectively used for the method for screening a therapeutic agent for asthma.

The present invention also provides a method for screening a therapeutic agent for asthma comprising the following steps:

1) treating test compounds or compositions to the kit for the diagnosis of asthma comprising the said DNA microarray or to the kit for the diagnosis of asthma comprising the primer set composed of the forward primer and the reverse primer which are complementary to NRP1 gene and at the same time capable of amplifying the said gene;

2) measuring NRP1 expression in the kit treated above in step 1); and 3) selecting test compounds or compositions demonstrating down-regulation of NRP1 by comparing the expression of NRP1 with that of the control.

In the zymography performed in this invention, NRP1 expression was increased in peripheral blood cells of asthma patients by TNF-α and the extract of D. pteronyssinus known to cause asthma. In the meantime, not only MMP-9 expression but also its functions such as enzyme activity and promoter activity were inhibited by NRP1 expression or activity inhibitor. Therefore, NRP1 gene was confirmed to be effectively used for the method for screening a therapeutic agent for asthma.

The present invention also provides a pharmaceutical composition for the treatment of asthma comprising NRP1 gene expression or activity inhibitor as an active ingredient.

The present invention also provides a method for the treatment of asthma comprising the step of administering a pharmaceutically effective dose of NRP1 gene expression or activity inhibitor to a subject with asthma.

In addition, the present invention provides NRP1 gene expression or activity inhibitor to be used as a pharmaceutical composition for the treatment of asthma.

The said NRP1 gene expression inhibitor is preferably selected from the group consisting of antisense nucleotide complementarily binding to NRP1 mRNA, short interfering RNA, and short hairpin RNA, but not always limited thereto. Among them, short interfering RNA and short hairpin RNA are more preferred, and short hairpin RNA is most preferred, but not always limited thereto.

The said NRP1 gene activity inhibitor can be selected from the group consisting of compound, peptide, peptide mimetics, and antibody which are complementarily binding to NRP1 protein, but not always limited thereto.

The subject herein can be mammals including human, but not always limited thereto.

In a preferred embodiment of the present invention, it was observed that NRP1 was expressed in peripheral blood cells of asthma patients, and the expression was increased by TNF-α and the extract of *D. pteronyssinus* known to cause asthma. It was also observed that MMP-9 expression and function were inhibited by NRP1 expression or activity inhibitor. Therefore, the relation between NRP1 gene and asthma was confirmed, suggesting that NRP1 expression or activity inhibitor can be effectively used as a pharmaceutical composition for the treatment of asthma since asthma related MMP-9 expression and function can be suppressed by NRP1 expression or activity inhibitor.

The pharmaceutically effective dosage of NRP1 expression or activity inhibitor of the present invention can be determined by considering various factors such as administration method, target area, patient condition, etc. Thus, the dosage for human body has to be determined with the consideration of safety and efficiency at the same time. It is also possible to predict the effective dosage based on the effective dosage for animal confirmed by animal test. Various factors that have to be considered for the determination of the effective dosage are described in the following articles: Hardman and Limbird, eds., Goodman and Gilman's The Pharmacological Basis of Therapeutics, 10th ed. (2001), Pergamon Press; and E. W. Martin ed., *Remington's Pharmaceutical Sciences,* 18th ed. (1990), Mack Publishing Co.

The pharmaceutical composition of the present invention can include any generally used carrier, diluent, excipient, or a combination of at least two of those. The pharmaceutically acceptable carrier can be any carrier that is able to deliver NRP1 expression or activity inhibitor of the present invention in human body without limitation, which is exemplified by the compounds described in Merck Index, 13th ed., Merck & Co. Inc., such as saline, sterilized water, Ringer's solution, buffered saline, dextrose solution, maltodextrin solution, glycerol, ethanol, liposome and a mixture comprising one or more of those components. If necessary, a general additive such as antioxidant, buffer, and bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. The composition can further be prepared in suitable forms according to ingredients by following the method represented in Remington's Pharmaceutical Science (Mack Publishing Company, Easton Pa., 18th, 1990).

The composition of the present invention can include, in addition to NRP1 expression or activity inhibitor, one or more effective ingredients having the same or similar function to NRP1 expression or activity inhibitor. The composition of the present invention can include the said protein by 0.0001-10 weight %, and preferably 0.001-1 weight % by the total weight of the composition.

The composition of the present invention can be administered orally or parenterally (for example, intravenous, hypodermic, peritoneal or local injection). The effective dosage of the composition can be determined according to weight, age, gender, health condition, diet, administration frequency, administration method, excretion and severity of a disease. The dosage is 0.0001~10 mg/ml per day and preferably 0.0001~5 mg/ml per day, and administration frequency is once a day or preferably a few times a day.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Cell Culture

<1-1> THP1 Cell Culture

THP1 cells, the human macrophage precursor cells, were cultured in DMEM (Life Technologies, U.S.A.) supplemented with 10% FBS, 100 units/nl of penicillin, and 100 μg/10 of streptomycin.

<1-2> HT-1080 Cell Line Culture

HT1080 cell line (ATCC CCL121), the human fibrosarcoma cell line, was cultured in DMEM (Life Technologies, U.S.A.) supplemented with 10% FBS, 100 units/la of penicillin, and 100 μg/ml of streptomycin.

<1-3> RAW 264.7 Cell Line Culture

RAW264.7 cell line, the mouse monocyte/macrophage cell line, was cultured in DMEM (Life Technologies, U.S.A.) supplemented with 10% FBS, 100 units/la of penicillin, 100 μg/ml of streptomycin, 6 g/l of HEPES, and 3.7 g/l of sodium bicarbonate in a $CO_2$ incubator (5% $CO_2$, 95% relative humidity, 37° C.).

Example 2

Construction of Vector for Luciferase Assay

To construct a reporter vector for the examination of MMP-9 transcription activity, oligonucleotides containing XhoI and HindIII sites, which were GATCCTCGAGCTAGAGGCTGCTACTTGC (SEQ. ID. NO: 4) and GATCAAGCTTTCTGACTGCAGCTGCTGT (SEQ. ID. NO: 5), were synthesized. Then, MMP-9 promoter region (−670/+3) was amplified by PCR using human cDNA as a template. As transcription reporters, the gene expressing luciferase and the reporter vector pGL4.14 (Promega) expressing hygromycin B phosphotransferase as a selection marker were used. The reporter vector was digested with XhoI and HindIII, and then conjugated to MMP-9 promoter region synthesized by PCR (−670/+3), leading to the construction of the reporter vector having human MMP-9 promoter region, pGL4.14-pMMP-9-Luc.

Example 3

Construction of Cell Line for Luciferase Assay

One day before transfection, HT1080 and RAW264.7 cells under the culture in DMEM were transferred to fresh medium, followed by culture for one more day. The vector pGL4.14-pMMP-9-Luc DNA was mixed well in FuGenelHD (Roche, USA) transfection buffer, which was then distributed to the cells evenly. After 6 hours of culture, the medium was replaced with fresh medium, followed by further culture for 2 days. Two days later, the cells were transferred to selection medium containing the antibiotics G418 at the concentration of 0.8 mg/ml at the ratio of 1:15. The medium was replaced with fresh medium every 4 days, during which formed colonies were collected and sub-cultured further. A part of the cells was stored in liquid nitrogen. Colonies of the cells that survived in DMEM supplemented with the antibiotics G418 at the concentration of 1 mg/ml were selected and as a result HT1080-pMMP-9-Luc cell line and RAW-pGL4-MMP-9-luc cell line were obtained.

HT1080 cells were treated with TNF-a (5 ng/ml) and RAW cells were treated with LPS (Lipopolysaccharides) (1 µg/ml). Compared with the non-treated cells, the cell line demonstrating high luciferase activity was selected. To identify the condition that increased luciferase activity, the above experiment was repeated with different cell concentrations.

Experimental Example 1

Measurement of NRP and Inflammatory Cytokine Expressions Induced by D. pteronissinus Extract THP1 cell line was treated with D. pteronissinus extract (purchased from Arthropods of Medical Importance Resource Bank, Yonsei University School of Medicine) at the concentrations of 0, 0.1, 1, 10, and 50 µg/ml. Then, inflammatory cytokine expression was investigated. Lipopolysaccharides (LPS) known to induce inflammatory cytokine expression was used as the positive control. After treating THP1 cell line with D. pteronissinus extract and lipopolysaccharides, mRNA expressions of interleukin 6 (IL6), interleukin 8 (IL8), monocyte chemoattractant protein 1 (MCP1), and neuropilin 1 (NRP1) were measured.

Particularly, 2 ml of THP1 cell culture solution was distributed in each well of 12 well plate at the density of $2\times10^6$ cells/ml, followed by stabilization for 24 hours. The cells were treated with the extract of D. pteronissinus, the most critical cause of asthma, at the concentrations of 10 µg/ml (low dose) and 50 µg/ml (high dose), followed by culture for 48 hours. To prepare the positive control, 1 µg/ml of LPS was treated. After 48 hours of culture, total RNA was extracted and purified by using RNeasy kit (Qiagen, Hilden, Germany) according to the manufacturer's protocol. Reverse transcription was performed with 1 µg of the total RNA using cDNA Reverse Transcription Kit (Applied Biosystems, Inc., Foster City, Calif., USA). Real-time PCR was carried out by using StepOne machine (Applied Biosystems, Inc., Foster City, Calif., USA). PCR was repeated three times with TaqMan gene expression master mix, 250 nM TaqMan Probe, 2 uM of each primer, and 2 µl of cDNA (total reaction volume was 20 µl). PCR tube containing the proper mixture composition was reacted at 95° C. for 10 minutes, followed by 40 cycles of reactions at 95° C. for 15 seconds and at 60° C. for 1 minute. The primers used for Real-Time PCR were purchased from Applied Biosystems Inc. (assay on demand gene expression, Applied Biosystems, Inc., Foster City, Calif., USA). The serial numbers are as follows:

IL6: Hs00174131_m1;
IL8: Hs99999034_m1;
MCP1: Hs00234140_m1; and
NRP1: Hs00818574_m1.
18s rRNA was used as the internal control:
18s rRNA: Hs99999901_s1.

Figure 1:
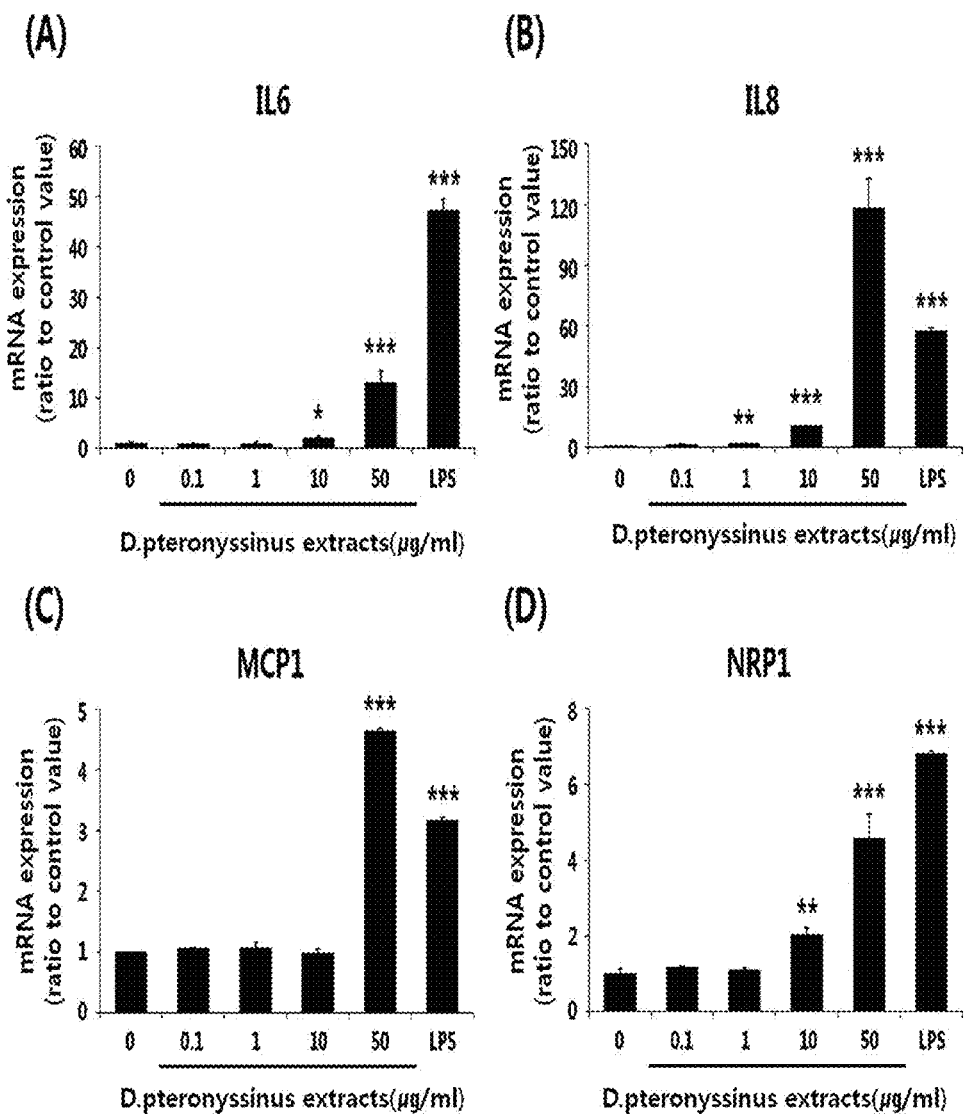
FIG. 1 is a set of graphs illustrating the increase of the expressions of NRP1 gene and inflammatory cytokines by *D. pteronissinus* extract.

As a result, when LPS used as the positive control was treated, the expressions of inflammatory cytokines such as IL6, IL8, and MCP1 were all increased. The expressions of 116 and IL8 were increased by the treatment of D. pteronissinus extract dose-dependently (FIGS. 1A and 1B). MCP1 expression was not much increased when D. pteronissinus extract was treated at the concentrations of 0.1~10 µg/ml (low dose), compared with the non-treated group, but significantly increased when the extract was treated at the concentration of 50 µg/ml (high dose) (FIG. 1C). As the concentration of D. pteronissinus extract was increased, NRP1 mRNA expression was significantly increased (FIG. 1D). Therefore, it was confirmed that the D. pteronissinus extract increased the expressions of inflammatory cytokines and NRP1 as well (FIG. 1).

Experimental Example 2

Measurement of Inflammatory Cytokine Expression Changes Induced by NRP1 siRNA

THP1 cell line was transfected with NRP1 siRNA and the control siRNA (si-control) respectively, to which D. pteronissinus extract (10, and 50 µg/ml and LPS were treated. Then, inflammatory cytokine expression changes were measured.

THP1 cell line was prepared in 12-well dish at the density of $2\times10^6$ cells/mL. NRP1 siRNA and control siRNA were purchased from Santacruz Co. and the serial numbers are as follows:

NRP1 siRNA: Santacruz, sc-36038; and
control siRNA: Santacruz, sc-37007.

The cells were treated with 60 M siRNA and Lipofectamin RNAiMAX reagent (Invitrogen, 12778) together for 6 hours. Then, D. pteronissinus extract and LPS were treated thereto at the proper concentrations, followed by culture for 48 hours. The cultured cells were used for real time PCR.

As a result, NRP1 mRNA expression was significantly reduced in the group transfected with NRP1 siRNA, compared with that in the control group transfected with the control siRNA. When the group transfected with NRP1 siRNA was treated with the extract of D. pteronissinus inducing the expressions of inflammatory cytokines, NRP1 expression was significantly reduced, compared with the control group treated with the control siRNA. Therefore, it was confirmed that NRP1 siRNA was working effectively (FIG. 1A). The expressions of inflammatory cytokines such as IL6, IL8, and MCP1 were increased as the concentration of D. pteronissinus extract increased, which was consistent with the results of <Experimental Example 1>. However, in the group treated with NRP1 siRNA, the expressions of those cytokines were significantly reduced, compared with the control group treated with the control siRNA (FIGS. 1A, 1B, 1C, and 1D).

Experimental Example 3

Measurement of NRP1 Expression in Peripheral Blood Cells of Asthma Patients mRNA was extracted from peripheral blood cells of normal control subjects and asthma patients, followed by comparison of NRP1 mRNA expression. The general characteristics of asthma patients volunteered in this experiment are shown in Table 1.

Asthma patients and normal control subjects were collected from Yongsan Hospital, Chung-Ang University School of Medicine, Seoul, Korea. Peripheral blood was drawn (10 cc/person) in fasting state. The blood sample was centrifuged at 3000 rpm for 15 minutes to separate buffy coat. Total RNA was extracted from the separated buffy coat by using RiboPure™ Blood Kit (Ambion) according to the manufacturer's protocol, followed by purification. The purified total RNA was stored at −80° C. Asthma patients were questioned about previous prescriptions or drug taking history including inhalers (steroids, beta 2 agonists, bronchidilators, etc) and oral preparations (steroids, theophylline, leukotriene regulators, beta 2 agonists, antihistamines, etc) for the past three months from the blood work. Those patients who first visited the hospital were grouped into non-administered patient group and peripheral blood was drawn from them.

As a result, NRP1 mRNA expression was significantly increased in peripheral blood cells of asthma patients, compared with the normal control group (FIG. 3A). Among asthma patients, the group (64 patients) administered with asthma drug in the past demonstrated significantly low NRP1 mRNA expression, compared with the group (8 patients) non-treated with any asthma drug before (FIG. 3B).

The present inventors also investigated NRP1 expression patterns over smoking. As shown in Table 1, 6 out of 34 control people were smoker, indicating 18.2% smoking rate. In the meantime, 16 out of 72 asthma patients were smokers, indicating 22.2% smoking rate (Table 1). NRP1 mRNA expression in the normal control group was not changed much over smoking (FIG. 4A). However, in the case of asthma patients, NRP1 mRNA expression was significantly increased in peripheral blood cells of smokers (FIG. 4B).

In addition, the present inventors investigated NRP1 expression patterns over the patient's medical history. Asthma patients had the history of tuberculosis, allergic rhinitis, atopic dermatitis, and urticaria. RNP1 mRNA expression was compared among those 4 kinds of diseases. As a result, as shown in Table 2, NRP1 expression was increased particularly in the patients who had the history of atopic dermatitis (P value<0.1) (Table 2).

TABLE 1

General characteristics of study subjects

|  | Control (n = 34) | Asthma (n = 72) | P-value |
|---|---|---|---|
| Gender Ratio (Male:Female) | 22:11 | 36:36 | 0.156[b] |
| Age | 46.97 ± 2.22[a] | 52.42 ± 1.77 | 0.083[c] |
| BMI(kg/m$^2$) | 24.42 ± 0.64 | 24.36 ± 0.36 | 0.324[d] |
| FEV1(L) | 3.04 ± 0.13 | 2.47 ± 0.10 | 0.006[d] |
| FEV1 (expected value %) | 90.04 ± 2.07 | 90.64 ± 2.74 | 0.030[d] |
| FVC(L) | 3.88 ± 0.16 | 3.58 ± 0.91 | 0.994[d] |
| FEV1/FVC(%) | 78.60 ± 1.26 | 68.71 ± 1.73 | 0.000[d] |
| Smoking (No:Yes(Smoker %)) | 28:6(18.2%) | 56:16(22.2%) | 0.762[d] |

[a]mean ± SE
[b]P-value obtained by Chi-square test.
[c]P-value obtained by ANOCOVA based on gender ratio.
[d]P-value obtained by ANOCOVA based on gender ratio and age.

TABLE 2

NRP1 mRNA expression patterns according to patient's medical history

| Medical history | No | Yes | P-value |
|---|---|---|---|
| Tuberculosis | 57(1.38 ± 0.08)[a] | 15(1.59 ± 0.29) | 0.148[b] |
| Allergic rhinitis | 51(1.42 ± 0.11) | 21(1.45 ± 0.16) | 0.853 |
| Atopic dermatitis | 65(1.37 ± 0.08) | 7(1.93 ± 0.52) | 0.098 |
| Urticaria | 60(1.42 ± 0.09) | 12(1.47 ± 0.30) | 0.948 |

[a]mean ± SE. NRP1 mRNA level was represented by ratio to mean value of the control.
[b]P-value obtained by ANOCOVA based on gender ratio and age.

Experimental Example 4

Measurement of MMP-9 Promoter Activity Changes by NRP1 Expression Inhibition siRNA vector against NRP1 gene was constructed as follows. NRP1 siRNA target primer was designed by using two kinds of siRNA target programs (http://www.promega.com/siRNADesigner/program; and http://www/genscript.com/ssl-bin/app/rnai). The siRNA target primer contained the forward sequence of CTGCACAAATCTCTGAAACTA (SEQ. ID. NO: 6) and was composed of 21 nucleotides having GC range of 30~60%. The siRNA target primer was located forwardly and reversely in order to form loop in the center. To be cloned in the vector easily, BamHI and HindIII sites were located in both ends. The siRNA target forward primer (SEQ. ID. NO: 7,5'-ATCCCGTAGTTTCAGAGATTTGTGCAGT-TGATATCCGCTGCACAAATCTCTGAAACTATTTT TTCCAAA-3') and the siRNA target reverse primer (SEQ. ID. NO: 8, 5'-AGCTTTTGGAAAAAATAGTTTCA-GAGATTTGTGCAGCGGATATCAACTGCA-CAAATCTCTGA AACTACGG-3') designed as such were purchased from Bioneer Co.

Scrambled siRNA contained the forward sequence of GGCGCGCTTTGTAGGATTCG (SEQ. ID. NO: 9) and also located forwardly and reversely in order to form loop in the center. To be cloned in the vector easily, BamHI and HindIII sites were located in both ends. The scrambled siRNA forward primer (SEQ. ID. NO: 10, 5'-GATCCCGCGAATC-CTACAAAGCGCGCTTGATATCCG-GCGCGCTTTGTAGGATTCGTTTTTTC CAAA-3') and the scrambled siRNA reverse primer (SEQ. ID. NO: 11, 5'-AGCTTTTGGAAAAAACGAATCCTA-CAAAGCGCGCCGGATAT-CAAGCGCGCTTTGTAGGATTC GCGG-3') designed as such were purchased from Bioneer Co. The purchased sequences were combined each other, followed by cloning into pRNAT-U6.1/NEO vector (purchased from Genescript) digested with BamHI and HindIII by using T4 ligase. The reaction product was introduced in E. coli DH5α. Colony PCR was performed using the forward and reverse primers detectable in pRNA-U6/Neo vector in order to obtain single clone inserted with siRNA target. DNA was extracted from the single clone inserted with siRNA target, followed by sequencing.

One day before transfection, RAW264.7 cell line harboring pGL4.14-pMMP9(−670/+3) vector useful for the measurement of MMP-9 promoter activity was distributed in 96-well plate at the density of $3\times10^4$ cells/well. 24 hours later the medium was replaced with FBS-free fresh DMEM. PRNAT-U6/neo vector, scrambled shRNA, and NRP1 shRNA were mixed in FuGenelHD transfection reagent (purchased from Roche Co.) according to the manufacturer's protocol, which was treated to the cells at different concentrations, followed by luciferase assay.

As a result, the longer the culture time of RAW264.7 cell line, the higher the MMP-9 promoter activity was. In the group treated with NRP1 shRNA, as treating time became longer (1.5, 3, and 6 h), MMP-9 expression was significantly decreased, compared with the group treated with the control vector, which was confirmed indirectly by measuring promoter activity (FIG. 5).

Experimental Example 5

Measurement of MMP-9 enzyme activity Induced by TNF-α

To examine MMP-9 enzyme activity, that is the gelatin degradation inhibitory activity, induced by TNF-α, the conditioned medium obtained from HT1080 cell culture medium treated with TNF-α at the concentrations of 5, 20, 50, and 100 ng/n1 was diluted in the buffer containing 62.5 mM Tris-HCl (pH 6.8), 10% glycerol, 2% SDS, and 0.00625% (w/v) bromophenol blue. The solution proceeded to electrophoresis on 10% polyacrylamide gel containing 0.1% (w/v) gelatin without heating. After the electrophoresis, the gel was washed with reaction buffer [1 M Tris-HCl (pH 7.5), 0.1 M NaCl, 2.5% Triton X-100] at room temperature for 30 minutes. Then, the gel in the reaction buffer [1 M Tris-HCl (pH 7.5), 10 mM $CaCl_2$] was loaded in each vessel. The prepared gel treated with TNF-alpha at different concentrations of 5, 20, 50, and 100 ng/n1 was incubated at 37° C. for 16 hours. The white band indicating enzyme activity was confirmed by coomassie brilliant blue G staining. The staining was destained in buffer containing ethanol and acetic acid.

HT1080 cells were treated with TNF-α at different concentrations of 5, 20, 50, and 100 μg/ml for 24 hours. Then, MMP-9 activity was measured by gelatin zymography. As a result, as shown in FIG. 6, MMP-9 enzyme activity was increased by TNF-α dose-dependently (FIG. 6).

Experimental Example 6

Measurement of the Effect of NRP1 siRNA in HT1080 Cell Line

To examine the effect of NRP1 siRNA in HT1080 cell line, the cell line was treated with NRP1 siRNA at different concentrations and PCR was performed to measure NRP1 mRNA expression.

Particularly, HT1080 cell line was treated with 5 nM, 10 nM, 20 nM, and 50 nM of NRP1 siRNA, and siNC (siRNA negative control), the negative control siRNA. After extracting RNA, PCR was performed to measure NRP1 expression. As a result, as shown in FIG. 7A, NRP1 expression was reduced by NRP1 siRNA dose-dependently (FIG. 7A). NRP1 expression was quantified based on the amount of beta-actin expression, and presented in the graph. As shown in FIG. 7B, NRP1 expression was reduced by NRP1 siRNA dose-dependently (FIG. 7B).

To investigate whether or not NRP1 siRNA could inhibit NRP1 protein expression efficiently in HT1080 cell line, 20 nM of NRP1 siRNA, confirmed to inhibit NRP1 mRNA expression effectively earlier in FIG. 7, was treated to HT1080 cell line. Then, protein expression was measured by Western blotting. Particularly, cell extract of HT1080 treated with 20 nM of NRP1 siRNA was prepared, and then MMP-9 expression was quantified by Western blotting. At this time, beta-actin was used as the internal control. The cells treated with 20 nM of NRP1 siRNA for 24 hours were lysed by using lysis buffer [50 mM Tris-HCl (pH 8.0), 150 mM NaCl, 1% NP-40, 0.25% Na-deoxycholate, 1 mM EDTA, 1 mM NaF, 1 mM Na $VO_4$, 1 mM PMSF, protease inhibitor cocktail (purchased from Calbiochem)]. Quantification of the protein in the cell extract was performed by using Bio-Rad protein quantification kit (Bio-Rad, USA). Protein extract was prepared by using the said protein extraction buffer, and 50 μg of each protein extract obtained from the control group and the group treated with NRP1 siRNA proceeded to electrophoresis on SDS-polyacrylamide gel. Upon completion of the electrophoresis, the protein was adsorbed on polyvinylidene difluoride membrane, followed by blocking with 5% skim milk for 2 hours. Then, the membrane was reacted with NRP1 and beta-actin antibody (purchased from Santa Cruz Co.). The antibody conjugated membrane was washed with TBST buffer and reacted with horseradish peroxidase labeled secondary antibody (purchased from Santa Cruz Co.). After washing the membrane with TBST buffer, protein detection was performed by using ECL system (Amersham Pharmacia Biotech).

As a result, as shown in FIG. 8, NRP1 protein expression in the group treated with NRP1 siRNA was significantly reduced, compared with that in the group treated with the negative control siNC (FIG. 8).

Experimental Example 7

Measurement of MMP9 expression changes Induced by NRP1 siRNA

To confirm the treatment effect of NRP1 on asthma, HT1080 cell line was treated with NRP1 siRNA and then treated with TNF-α known to be critically involved in asthma, followed by investigation of MMP-9 and NRP1 expressions.

Particularly, HT1080 cells were treated with NRP1 siRNA at different concentrations, followed by treatment with TNF-α. Then, MMP-9 mRNA expression was compared. As a result, MMP-9 expression increased by TNF-α was significantly reduced by the treatment of NRP1 siRNA (FIG. 9A). In addition, MMP-9 expression was quantified based on the amount of beta-actin expression, and presented in the graph. As a result, MMP-9 expression was reduced by NRP1 siRNA dose-dependently (FIG. 9B).

To confirm whether or not NRP1 siRNA could inhibit MMP-9 and NRP1 protein expressions, HT1080 cells were treated with NRP1 siRNA and then treated with 20 ng/ml of TNF-α as well. Western blotting was performed to quantify NRP1 and MMP-9 protein expressions. The experiment with beta-actin and NRP1 was performed by the same manner as described in <Experimental Example 8>. MMP-9 protein expression was quantified by the same manner as described above after collecting the cell culture medium. Protein extract was prepared using the same buffer. The experiment processes were the same as described in <Experimental Example 7>, for which MMP-9 antibody (purchased from Santa Cruz Co.) was used.

As a result, as shown in FIG. 10, MMP-9 and NRP1 protein expressions were all increased by the treatment of TNF-α. In the meantime, MMP-9 and NRP1 protein expressions were significantly reduced by the treatment of NRP1 siRNA dose-dependently (FIG. 10).

Experimental Example 8

Measurement of MMP9 enzyme activity Changes induced by NRP1 siRNA

It was observed that MMP-9 expression that had been increased by TNF-α in HT1080 cells was significantly reduced after the treatment of NRP1 siRNA. To confirm whether or not NRP1 siRNA treatment could reduce not only MMP-9 expression but also the functions thereof, the present inventors performed gelatin zymography to measure MMP-9 enzyme activity. Particularly, HT1080 cells were treated with NRP1 siRNA and the negative control siNC at the concentrations of 5, 10, and 20 nM, followed by the treatment with 5 ng/ml of TNF-α for 24 hours. The conditioned medium obtained from HT1080 cell culture medium was diluted in the buffer containing 62.5 mM Tris-HCl (pH 6.8), 10% glycerol, 2% SDS, and 0.00625% (w/v) bromophenol blue. The experiment processes were the same as those for zymography.

As a result, as shown in FIG. 11, MMP enzyme activity induced by TNF-α in HT1080 cells was reduced by the treatment of NRP1 siRNA dose-dependently (FIG. 11).

Experimental Example 9

Measurement of MMP-9 promoter activity Changes induced by NRP1 siRNA

To investigate MMP-9 promoter activity changes by the suppression of NRP1 expression or activity, pGL-MMP-9 vector useful for the measurement of MMP-9 promoter activity was constructed. Then, MMP-9 promoter activity was measured by using HT1080 cell line harboring the said vector (FIG. 12). The HT1080 cell line harboring pGL4.14-pMMP-9(−670/+3) vector constructed in Example 3 was cultured in DMEM supplemented with 0.1 mg/ml of hygromycin B. Then, the cells were detached by using trypsin solution and the density was adjusted to be $3 \times 10^4$ cells/ml. The cells were loaded in each well of 96-well white with clear bottom plate (purchased from Costar Co.) by 100 μl, followed by culture in a 37° C. $CO_2$ incubator for 24 hours. The cells were washed with PBS and the medium was replaced with FBS-free fresh DMEM. Non-treated control group, siNC treated negative control group, and NPR1 siRNA treated groups each treated with NRP1 siRNA at the different concentrations of 5, 10, and 20 nM were prepared. Each group was treated with siRNA and the control siNC for one hour, and treated with 5 ng/nl of TNF-α, followed by further culture for 24 hours. The supernatant was eliminated and the cells were washed with PBS. The cells were lysed by using 40 μl of luciferase lysis buffer (purchase from Promega). Luciferase assay reagent (purchased from Promega) was added to the 96-well plate containing the cell lysate. Then, MMP-9 promoter activity was measured by using luminometer.

As a result, as shown in FIG. 13, similarly to MMP-9 mRNA and protein expressions, MMP-9 promoter activity that had been increased by TNF-α was reduced by the treatment of NRP1 siRNA dose-dependently, suggesting that the decrease was getting significant as the concentration of NRP1 siRNA was increased from 5 nM to 10 nM and 20 nM (FIG. 13).

The Manufacturing Examples of the composition for the present invention are described hereinafter.

Manufacturing Example 1

Preparation of Pharmaceutical Formulations

<1-1> Preparation of Powders

| NRP1 expression or activity inhibitor | 2 g |
| Lactose | 1 g |

Powders were prepared by mixing all the above components, which were filled in airtight packs according to the conventional method for preparing powders.

<1-2> Preparation of Tablets

| NRP1 expression or activity inhibitor | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| NRP1 expression or activity inhibitor | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| NRP1 expression or activity inhibitor | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| NRP1 expression or activity inhibitor | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

INDUSTRIAL APPLICABILITY

As explained hereinbefore, the present invention disclosed the relation between NRP1 gene and asthma for the first time. NRP1 gene expression or activity inhibitor reduced inflammatory cytokine expression and MMP-9 activity, so that it can be effectively used for the kit for the diagnosis of asthma and for the screening of a therapeutic agent for asthma using the same.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for inhibiting the expression or activity of Matrix metallopeptidase 9s (MMP-9s) comprising:
   administering an effective dose of NRP1 (neuropilin 1) gene expression or activity inhibitor to a cell, and
   inhibiting the expression or activity of MMP-9s,
   wherein the NRP1 gene expression or activity inhibitor is selected from the group consisting of antisense nucleotides binding complementarily to NRP1 mRNA, NRP1 short interfering RNA and NRP1 short hairpin RNA,
   wherein the cell is a human acute monocytic leukemia cell, a human peripheral blood cell.

2. The method of claim 1, wherein the NRP1 gene consists of the nucleotide sequence of SEQ ID NO: 1.

3. A method for inhibiting the expression or activity of Matrix metallopeptidase 9s (MMP-9s) comprising:
   treating a cell with an effective dose of NRP1 (neuropilin 1) short interfering RNA, and
   inhibiting the expression or activity of MMP-9s,
   wherein the cell is a human acute monocytic leukemia cell, a human peripheral blood cell.

4. The method of claim 1, wherein the method is carried out in vitro.

5. The method of claim 3, wherein the method is carried out in vitro.

* * * * *